US009040073B2

(12) United States Patent
Boison et al.

(10) Patent No.: US 9,040,073 B2
(45) Date of Patent: May 26, 2015

(54) SILK POLYMER-BASED ADENOSINE RELEASE: THERAPEUTIC POTENTIAL FOR EPILEPSY

(75) Inventors: Detlev Boison, Portland, OR (US); David L. Kaplan, Concord, MA (US)

(73) Assignee: Trustees of Tufts College, Medford, MA (US)

( * ) Notice: Subject to any disclaimer, the term of this patent is extended or adjusted under 35 U.S.C. 154(b) by 275 days.

(21) Appl. No.: 12/991,973

(22) PCT Filed: May 15, 2009

(86) PCT No.: PCT/US2009/044117
§ 371 (c)(1),
(2), (4) Date: Jan. 28, 2011

(87) PCT Pub. No.: WO2009/140588
PCT Pub. Date: Nov. 19, 2009

(65) Prior Publication Data
US 2011/0152214 A1    Jun. 23, 2011

Related U.S. Application Data

(60) Provisional application No. 61/053,413, filed on May 15, 2008.

(51) Int. Cl.
A61K 31/70    (2006.01)
A61F 2/00    (2006.01)
A01N 43/04    (2006.01)
A61K 9/00    (2006.01)
A61K 47/42    (2006.01)

(52) U.S. Cl.
CPC .............. *A61K 9/0085* (2013.01); *A61K 47/42* (2013.01)

(58) Field of Classification Search
CPC ............................ A61K 47/42; A61K 9/0085
See application file for complete search history.

(56) References Cited

U.S. PATENT DOCUMENTS

| | | | |
|---|---|---|---|
| 1,989,005 A | 1/1935 | Fink et al. | |
| 4,233,212 A | 11/1980 | Otoi et al. | |
| 4,820,418 A | 4/1989 | Hirotsu et al. | |
| 5,047,507 A | 9/1991 | Buchegger et al. | |
| 5,290,494 A | 3/1994 | Coombes et al. | |
| 5,606,019 A | 2/1997 | Cappello | |
| 5,728,810 A | 3/1998 | Lewis et al. | |
| 5,770,193 A | 6/1998 | Vacanti et al. | |
| 5,994,099 A | 11/1999 | Lewis et al. | |
| 6,110,590 A | 8/2000 | Zarkoob et al. | |
| 6,110,902 A * | 8/2000 | Mohler et al. | 514/46 |
| 6,123,819 A | 9/2000 | Peeters | |
| 6,175,053 B1 | 1/2001 | Tsubouchi | |
| 6,592,623 B1 | 7/2003 | Bowlin et al. | |
| 6,815,427 B2 | 11/2004 | Tsubouchi et al. | |
| 6,902,932 B2 | 6/2005 | Altman et al. | |
| 7,041,797 B2 | 5/2006 | Vollrath | |
| 7,057,023 B2 | 6/2006 | Islam et al. | |
| 7,285,637 B2 | 10/2007 | Armato et al. | |
| 7,635,755 B2 | 12/2009 | Kaplan et al. | |
| 7,662,409 B2 | 2/2010 | Masters | |
| 7,674,882 B2 | 3/2010 | Kaplan et al. | |
| 7,727,575 B2 | 6/2010 | Kaplan et al. | |
| 7,842,780 B2 | 11/2010 | Kaplan et al. | |
| 7,960,509 B2 | 6/2011 | Kaplan et al. | |
| 8,071,722 B2 | 12/2011 | Kaplan et al. | |
| 8,585,753 B2 * | 11/2013 | Scanlon et al. | 623/1.42 |
| 2002/0028243 A1 | 3/2002 | Masters | |
| 2003/0007991 A1 | 1/2003 | Masters | |
| 2003/0183978 A1 | 10/2003 | Asakura | |
| 2004/0005363 A1 | 1/2004 | Tsukada et al. | |
| 2004/0266992 A1 | 12/2004 | Migliaresi et al. | |
| 2005/0220853 A1 | 10/2005 | Dao et al. | |
| 2007/0207186 A1 | 9/2007 | Scanlon et al. | |
| 2007/0212730 A1 | 9/2007 | Vepari et al. | |
| 2008/0085272 A1 | 4/2008 | Kaplan et al. | |
| 2008/0293919 A1 | 11/2008 | Kaplan et al. | |
| 2009/0202614 A1 | 8/2009 | Kaplan et al. | |
| 2009/0232963 A1 | 9/2009 | Kaplan et al. | |
| 2009/0234026 A1 | 9/2009 | Kaplan et al. | |
| 2010/0028451 A1 | 2/2010 | Kaplan et al. | |
| 2010/0046902 A1 | 2/2010 | Kaplan et al. | |
| 2010/0055438 A1 | 3/2010 | Kaplan et al. | |
| 2010/0063404 A1 | 3/2010 | Kaplan et al. | |
| 2010/0065784 A1 | 3/2010 | Kaplan et al. | |
| 2010/0068740 A1 | 3/2010 | Kaplan et al. | |
| 2010/0070068 A1 | 3/2010 | Kaplan et al. | |

(Continued)

FOREIGN PATENT DOCUMENTS

CA    2405850    10/2002
EP    0 496 617 B1 *  12/1999

(Continued)

OTHER PUBLICATIONS

Uebersax et al., "The Support of Adenosine Release from Adenosine-Kinase Deficient ES Cells by Silk Substrates," Biomaterials, 27, 4599-4607 (May 18, 2006).*
Boison et al., "Seizure Suppression in Kindled Rats By Intraventricular Grafting of an Adenosine Releasing Synthetic Polymer," Experimental Neurology, 160(1), 164-174 (1999).*
Li et al., Brain, 130:1276-1288 (2007). "Suppression of kindling epileptogenesis by adenosine releasing stem cell-derived brain implants."
Agarwal et al., Journal of Applied Polymer Science, 63(3):401-410 (1997). "Effect of Moisture Absorption on the Thermal Properties of *Bombyx mori* Silk Fibroin Films."
Asakura et al., Macromolecules, 17:1075-1081 (1984). NMR of silk fibroin 2. 13C NMR study of the chain dynamics and solution structure of *Bombyx mori* silk fibroin.

(Continued)

*Primary Examiner* — Lawrence E Crane
(74) *Attorney, Agent, or Firm* — Choate, Hall & Stewart LLP

(57) ABSTRACT

The invention provides formulations comprising adenosine in a silk fibroin-based, sustained-release delivery system. The formulations provide sustained, focal release of adenosine at therapeutic levels for the treatment of epilepsy and/or the prevention of epileptogenesis.

12 Claims, 13 Drawing Sheets

(56) References Cited

U.S. PATENT DOCUMENTS

| | | |
|---|---|---|
| 2010/0096763 A1 | 4/2010 | Kaplan et al. |
| 2010/0120116 A1 | 5/2010 | Kaplan et al. |
| 2010/0178304 A1 | 7/2010 | Wang et al. |
| 2010/0191328 A1 | 7/2010 | Kaplan et al. |
| 2010/0196447 A1 | 8/2010 | Kaplan et al. |
| 2011/0046686 A1 | 2/2011 | Kaplan et al. |
| 2011/0076384 A1 | 3/2011 | Cannizzaro et al. |
| 2011/0135697 A1 | 6/2011 | Omenetto et al. |
| 2011/0152214 A1 | 6/2011 | Boison et al. |
| 2011/0171239 A1 | 7/2011 | Kaplan et al. |
| 2012/0121820 A1 | 5/2012 | Kaplan et al. |
| 2012/0123519 A1 | 5/2012 | Lovett et al. |

FOREIGN PATENT DOCUMENTS

| | | |
|---|---|---|
| EP | 1440088 | 7/2004 |
| GB | 1182153 | 2/1970 |
| JP | 55-139427 | 10/1980 |
| JP | 60-142259 | 7/1985 |
| JP | 60-259677 | 12/1985 |
| JP | H01-254621 A | 10/1989 |
| JP | 01118544 | 11/1989 |
| JP | 06-346314 | 12/1994 |
| JP | 08-295697 | 11/1996 |
| JP | 10-36676 | 2/1998 |
| JP | 2000-273264 | 10/2000 |
| JP | 2003192807 | 7/2003 |
| JP | 2004068161 | 3/2004 |
| WO | 99/01089 | 1/1999 |
| WO | 01/36531 | 5/2001 |
| WO | 01/56626 | 8/2001 |
| WO | 02/072931 | 9/2002 |
| WO | 03/022909 | 3/2003 |
| WO | 03/038033 | 5/2003 |
| WO | 04/000915 | 12/2003 |
| WO | 2004/041845 | 5/2004 |
| WO | 2005012606 | 2/2005 |
| WO | 2005/123114 | 12/2005 |
| WO | 2008/118133 A3 | 10/2008 |
| WO | 2008/127405 | 10/2008 |
| WO | WO 2008/118133 A2 * | 10/2008 |
| WO | 2011/006133 | 1/2011 |

OTHER PUBLICATIONS

Asakura et al., Macromolecules, 18:1841-1845 (1985). "Conformational characterization of *B. mori* silk fibroin in the solid state by high-frequency 13C cross polarization-magic angel spinning NMR, X-ray diffraction and infrared spectroscopy."

Chen et al., J Appl Polymer Sci, 65:2257-2262 (1997). "pH sensitivity and ion sensitivity of hydrogels based on complex-forming chitosan/silk fibroin interpenetrating polymer network."

Chen et al., J Appl Polymer Sci, 73:975-980 (1999). "Separation of alcohol-water mixture by pervaporation through a novel natural polymer blend membrane-chitosan/silk fibroin blend membrane—chitosan / silk fibroin blend membrane."

Chen et al., Proteins: Structure, Function, and Bioinformatics, 68:223-231 (2007). "Conformation transition kinetics of *Bombyx mori* silk protein."

Database WPI Week 198205, Derwent Publications Ltd., London, GB AN 1982-09092E & JP 56 166235 A Dec. 21, 1981. Abstract.

Demura et al., Biosensors, 4:361-372 (1989). "Immobilization of biocatalysts with *Bombyx mori* silk fibroin by several kinds of physical treatment and its application to glucose sensors."

Demura et al., J Membrane Science, 59: (1991). "Porous membrane of *Bombyx mori* silk fibroin: structure characterization, physical properties and application to glucose oxidase immobilzation," (pp. 39-52).

Derwent Record, Abstract of JP 08295697 A2 "Production of aqueous solution of silk fibroin at high concentration." Nov. 12, 1996.

Doshi et al. J Electrostatics, 35:151-160 (1995). "Electrospinning process and applications of electrospun fibers."

Freddi et al., J Appl Polymer Sci, 56:1537-1545 (1995). "Silk fibroin/cellulose blend films: preparation, structure, and physical properties."

Hijirida et al., Biophysical Journal, 71:3442-3447 (1996). "13C NMR of *Nephila clavipes* major ampullate silk gland."

Hinman et al., TIBTECH, 18:374-379 (2000). "Synthetic spider silk: a modular fiber."

Hu et al., Biomacromolecules, 12:1686-1696 (2011). "Regulation of Silk Material Structure by Temperature-Controlled Water Vapor Annealing."

Huang et al., J Biomater Sci Polymer Edn, 12(9):979-993 (2001). "Engineered collagen-PEO nanofibers and fabrics."

Huang et al., Macromolecules, 33:2989-2997 (2000). "Generation of synthetic elastin-mimetic small diameter fibers and fiber networks."

Jin et al., Biomacromolecules, 3:1233-1239 (2002). "Electrospinning Bombyx mori silk with poly(ethylene oxide)."

Jin et al., Adv. Funct. Mater., 15:1241-1247 (2005). "Water-Stable Silk Films with Reduced β-Sheet Content."

Kweon et al., J Appl Polymer Sci, 80:1848-1853 (2001). "Preparation of semi-interpenetrating polymer networks composed of silk fibroin and poly(ethylene glycol) macromer."

Lazaris, Science, 295:472-476 (2002). "Spider silk fibers spun from soluble recombinant silk produced in mammalian cells."

Liang et al., J Appl Polymer Sci, 45:1937-1943 (1992). "Improvements of the physical properties of fibroin membranes with sodium alginate."

Lu et al., Acta Biomater. 6(4):1380-1387 (2010). "Water-Insoluble Silk Films with Silk I Structure."

Megeed et al., Pharmaceutical Research, 19(7):954-959 (2002). "Controlled release of plasmid DNA from a genetically engineered silk-elastinlike hydrogel."

Petrini et al., Journal of Materials Science: Materials in Medicine, 12:849-853 (2001). "Silk fibroin-polyurethane scaffolds for tissue engineering."

Reneker et al., Nanotechnology, 7:216-223 (1996). "Nanometre diameter fibres of polymer, produced by electrospinning."

Sawyer et al., JAMA, 191(9):740-742 (1965). "Dextran therapy in thrombophlebitis." Abstract.

U.S. Appl. No. 60/906,509, filed Mar. 13, 2007 by Omenetto et al.

U.S. Appl. No. 61/224,618, filed Jul. 10, 2009 by Numata et al.

Wang et al., Langmuir, 21:11335-11341 (2005). "Biomaterial coatings by stepwise deposition of silk fibroin."

Yamada et al., Thin Solid Films, 440:208-216 (2003). "AFM observation of silk fibroin on mica substrates: morphologies reflecting the secondary structure."

Zhou et al., Chem Commun, 2518-2519 (2001). "Preparation of a novel core-shell nanostructured gold colloid-silk fibroin bioconjugate by the protein in situ redox technique at room temperature."

Altman et al., Biomaterials, 24:401-416 (2003). "Silk-based biomaterials."

Anschel et al., Experimental Neurology, 190:544-547 (2004). "Focally injected adenosine prevents seizures in the rat."

Bekar et al., Nature Medicine, 14(1):75-80 (2008). "Adenosine is crucial for deep brain stimulation-mediated attenuation of tremor."

Boison et al., Experimental Neurology, 160:164-174 (1999). "Seizure Suppression in Kindled Rats by Intraventricular Grafting of an Adenosine Releasing Synthetic Polymer."

Boison, Future Neurol., 3(3):221-224 (2008). "Astrogliosis and adenosine kinase: a glial basis of epilepsy."

Boisin, Neurodegenerative Diseases, 4:28-33 (2007). "Adenosine-Based Cell Therapy Approaches for Pharmacoresistant Epilepsies."

Boison, Current Neuropharmacology, 5:115-125 (2007). "Cell and Gene Therapies for Refractory Epilepsy."

Boison, Progress in Neurobiology, 84:249-262 (2008). "The adenosine kinase hypothesis of epileptogenesis."

Dehdashti et al., Neurosurg Focus, 11(5):e6 (2001). "Preoperative silk suture embolization of cerebral and dural arteriovenous malformations."

Dulla et al., Neuron, 48:1011-1023 (2005). "Adenosine and ATP Link Pco2 to Cortical Excitability via pH."

Duncan et al., Lancet, 367:1087-1100 (2006). "Adult Epilepsy."

(56) References Cited

OTHER PUBLICATIONS

Dunwiddie et al., Annu. Rev. Neurosci., 24 Ann:31-55 (2001). "The Role and Regulation of Adenosine in the Central Nervous System."
Fedele et al., Experimental Neurology, 200:184-190 (2006). "Adenosine A1 receptors are crucial in keeping an epileptic focus localized."
Fredholm et al., Annu. Rev. Pharmacol. Toxicol., 45:385-412 (2005). "Actions of Adenosine at its Receptors in the CNS: Insights from Knockouts and Drugs."
Fredholm et al., International Review of Neurobiology, 63:191-270 (2005). "Adenosine and Brain Function."
Gouder et al., Epilepsia, 44(7):877-885 (2003). "Seizure Suppression by Adenosine A1 Receptor Activation in a Mouse Model of Pharmacoresistant Epilepsy."
Guttinger et al., Experimental Neurology, 193:53-64 (2005). "Seizure suppression and lack of adenosine A1 receptor desensitization after focal long-term delivery of adenosine by encapsulated myoblasts."
Guttinger et al., Epilepsia, 46(8):1162-1169 (2005). "Suppression of Kindled Seizures by Paracrine Adenosine Release from Stem Cell-Derived Brain Implants."
Hofmann et al., Journal of Controlled Release, 111:219-227 (2006). "Silk fibroin as an organic polymer for controlled drug delivery."
Horan et al., Biomaterials, 26:3385-3393 (2005). "In vitro degradation of silk fibroin."
Huber et al., PNAS, 98(13):7611-7616 (2001). "Grafts of adenosine-releasing cells suppress seizures in kindling epilepsy."
Jacobson et al., Nature Reviews Drug Discovery, 5:247-264 (2006). "Adenosine receptors as therapeutic targets."
Jin et al., Nature, 424:1057-1061 (2003). "Mechanism of silk processing in insects and spiders."
Karageorgiou et al., J. Biomed. Mater. Res.A 71(3):528-537 (2004). "Bone morphogenetic protein-2 decorated silk fibroin films induce osteogenic differentiation of human bone marrow stromal cells."
Kochanek et al., Journal of Cerebral Blood Flow & Metabolism, 26:565-575 (2006). "Adenosine A1 receptor knockout mice develop lethal status epilepticus after experimental traumatic brain injury."
Kohling, Klin Neurophysiol 37:216-224 (2006). "Pathophysiologie der Epilepsie."
Li et al., Biomaterials 27:3115-3124 (2006). "Electrospun silk-BMP-2 scaffolds for bone tissue engineering."
Li, et al., Brain 130:1276-1288 (2007). "Suppression of kindling epileptogenesis by adenosine releasing stem cell-derived brain implants."
Li et al., Neuron Glia Biology, 3(4):353-366 (2007). "Adenosine dysfunction in astrogliosis: cause for seizure generation?"
Li et al., The Journal of Clinical Investigation, 118(2):571-582 (2008). "Adenosine kinase is a target for the prediction and prevention of epileptogenesis in mice."
Loscher et al., Trends Neurosci 31(2):62-73 (2008). "Cell and gene therapies in epilepsy- promising avenues or blind alleys?"
Nilsen et al., Brain Research Reviews, 44:141-153 (2004). "Focal treatment for refractory epilepsy: hope for the future?"
Noe, et al., Peptides, 28:377-383 (2007). "Gene therapy in epilepsy: The focus on NPY."
Pitkanen et al., Epilepsia, 48(Suppl. 2):13-20 (2007). "Epileptogenesis in Experimental Models."
Raedt et al., Seizure-Eur 16:565-578 (2007). "Cell therapy in models for temporal lobe epilepsy."
Rebola et al., European Journal of Neuroscience 18:820-828 (2003). "Decrease of adenosine A1 receptor density and of adenosine neuromodulation in the hippocampus of kindled rats."
Schmutz et al., AJNR Am. J. Neuroradiol. 18:1233-1237 (1997). "Embolization of Cerebral Arteriovenous Malformations with Silk: Histopathologic Changes and Hemorrhagic Complications."
Shetty et al., Stem Cells, 25:2396-2407 (2007). "Concise Review: Prospects of Stem Cell Therapy for Temporal Lobe Epilepsy."
Sofia et al., Journal of Biomedical Materials Research, 54:139-148 (2001). "Functionalized silk-based biomaterials for bone formation."
Trayer et al., Biochem J., 139:609-623 (1974). "Preparation of Adenosine Nucleotide Derivatives Suitable for Affinity Chromatography."
Wang et al., Biomaterials, 28:4161-4169 (2007). "Silk coatings on PLGA and alginate microspheres for protein delivery."
Wang et al., Journal of Controlled Release, 117:360-370 (2007). "Silk microspheres for encapsulation and controlled release."
Wang et al., Biomaterials, 29:3415-3428 (2008). "In vivo degradation of three-dimensional silk fibroin scaffolds."
Wilz, et al., Biomaterials 29:3609-3616 (2008). "Silk polymer-based adenosine release: Therapeutic potential for epilepsy."
Extended European Search Report for EP 09 74 7669.1, 7 pages (Sep. 17, 2013).
International Search Report for PCT/US2009/044117, 2 pages (Jun. 29, 2009).
Written Opinion for PCT/US2009/044117, 6 pages (Jun. 29, 2009).

* cited by examiner

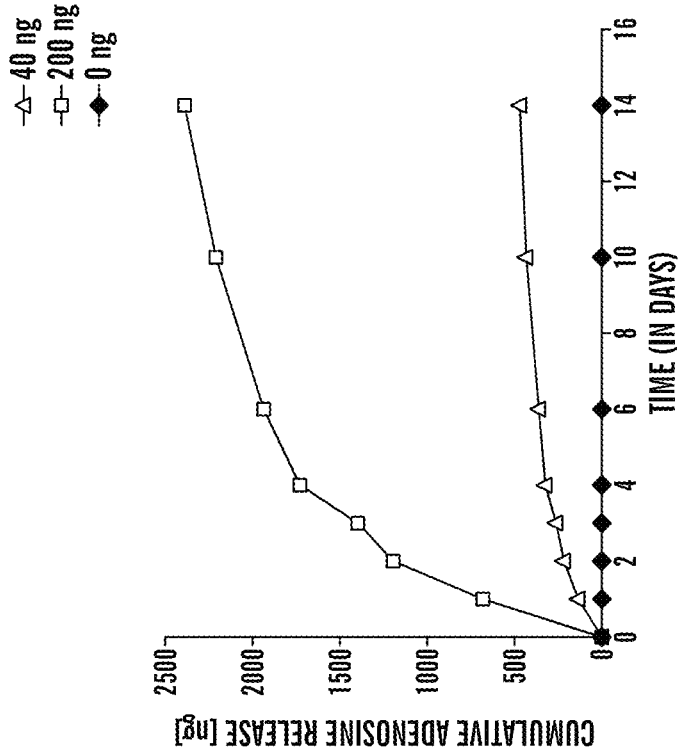
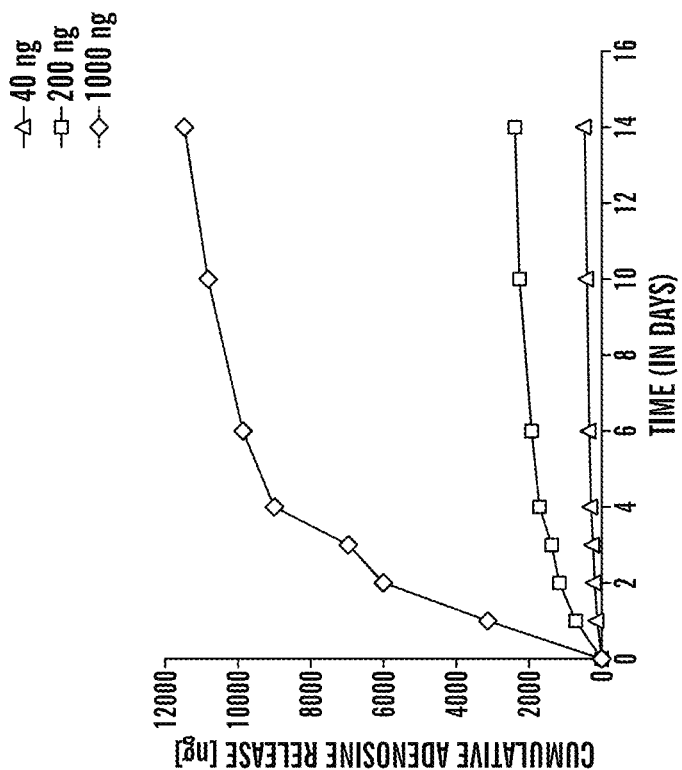
FIG. 2A
FIG. 2B

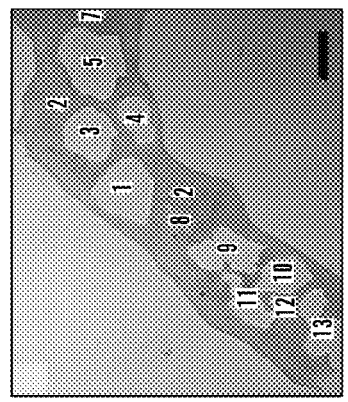
*FIG. 11A*
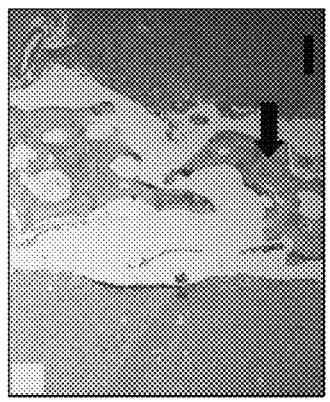
*FIG. 11B*
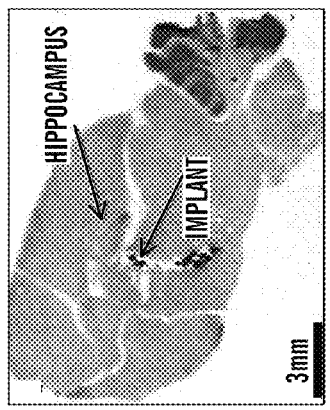
*FIG. 11D*
*FIG. 11C*

US 9,040,073 B2

SILK POLYMER-BASED ADENOSINE RELEASE: THERAPEUTIC POTENTIAL FOR EPILEPSY

CROSS REFERENCE TO RELATED PATENT APPLICATIONS

This application is a 35 U.S.C. §371 National Phase Entry application of International Application No. PCT/US2009/044117 filed on May 15, 2009, which designates the United States, and which claims benefit under 35 U.S.C. §119(e) of U.S. Patent Application Ser. No. 61/053,413, filed May 15, 2008, the contents of which are incorporated herein by reference in their entirety.

This invention was made with U.S. government support under grant number R01NS058780 awarded by the National Institute of Neurological Disorders and Stroke. The U.S. government has certain rights in the invention.

FIELD OF THE INVENTION

This invention relates to sustained release formulations. More specifically, the present invention relates to formulations comprising silk fibroin biopolymer and adenosine, that provides for sustained, focal release of adenosine at therapeutic levels for the treatment of epilepsy and/or the prevention of epileptogenesis.

BACKGROUND

Epilepsy is defined as the repeated occurrence of unprovoked seizures. One of the most common neurological disorders, epilepsy affects approximately 2.5 million Americans of all ages and backgrounds, and more than 60 million people worldwide. Based on modest estimates, at least one third of individuals diagnosed with epilepsy suffer from pharmacoresistance and intolerable side effects. Additionally, current antiepileptic drugs do little to prevent development of epilepsy (i.e., epileptogenesis) or to modify the progression of epilepsy. Therefore, therapeutic alternatives are urgently needed.

In contrast to systemic drug delivery, focal drug delivery to the brain is generally devoid of systemic side effects and holds promise for the therapy of epilepsy, which is frequently of focal origin. The recent identification of focal adenosine deficiency as major cause for seizure generation provides a neurochemical rationale for focal adenosine augmentation therapies (AATs). Focal AATs can be accomplished by implanting adenosine releasing devices or cells into the vicinity of an epileptogenic focus. AATs are devoid of systemic and sedative side effects, and augmentation of the adenosine response can suppress experimental seizures otherwise refractory to standard antiepileptic drugs. Thus, AATs hold promise for the therapy of refractory focal epilepsies. The experimental AATs are not suitable for clinical development, however, due to the use of animal cells or the short-term duration of therapeutic effect in some of the approaches. Further clinical development of AATs calls for the slow and sustained release of adenosine from safe and biocompatible brain implants.

SUMMARY

The present embodiments provide for silk biopolymer implants that deliver sustained release adenosine, administering focal therapy for the treatment of epilepsy. The silk fibroin-based adenosine-delivery formulations of the present embodiments exert potent anti-ictogenic effects, and at least partial anti-epileptogenic effects.

Adenosine augmentation therapies (AAT) make rational use of the brain's adenosine-based seizure control system and hold promise for the therapy of refractory epilepsy. Providing for an AAT compatible with clinical application, the present embodiments employ a novel silk protein-based release system for adenosine. In some aspects, adenosine-releasing brain implants with target release doses of 0 ng, 40 ng, 200 ng, and 1,000 ng adenosine per day were prepared by embedding adenosine-containing microspheres into nanofilm-coated silk fibroin scaffolds. In vitro, the respective polymers released 0 ng, 33.4 ng, 170.5 ng, and 819.0 ng adenosine per day over fourteen days. In a particular embodiment, the silk fibroin implant was designed to release about 1000 ng adenosine per day during a time span of ten days. This implant proved a safe and efficient therapy to suppress seizures.

The therapeutic potential of the implants was also validated in a dose-response study in a rat model of kindling epileptogenesis. For example, four to eight days prior to the onset of kindling, adenosine-releasing polymers were implanted into the infrahippocampal cleft, and progressive acquisition of kindled seizures was monitored over thirty stimulations. The present formulations provided a dose-dependent retardation of seizure acquisition. In recipients of polymers releasing about 819 ng adenosine per day, kindling epileptogenesis was delayed by more than one week. Histological analysis of brain samples confirmed the correct location of implants. Additionally, blockade of adenosine $A_1$ receptors did not exacerbate seizures in protected animals.

Another embodiment of the present invention provides for the prevention or treatment of epilepsy in a subject, including a human subject, by implanting a silk fibroin-based adenosine-releasing composition directly into the brain of the subject. The adenosine dose of the implant may be from about 50 ng/day to about 50 mg/day, inclusive, depending on size of the subject's hippocampus, the size of the epileptic focus, and in implantation site. For example, a lower dose may be required if the implant is placed directly into the epileptic focus; a higher dose may be required if the implant is placed into the ventricular system in the vicinity of the epileptic focus.

The length of time over which adenosine is delivered may be from about one month to over one year, inclusive. For example, short term delivery, e.g., one month following an epileptogenesis-triggering event, such as a traumatic brain injury, may prevent epileptogenesis. Because epilepsy is typically a permanent disease, a therapeutic implant system may be used to provide seizure control during the lifetime of a subject. Thus, an embodiment of the present invention provides for an implant system in which the silk-fibroin adenosine implant delivers adenosine for about one year, after which any expired scaffold is removed and replaced with a fresh implant, which system may be achieved via permanently implanted catheters.

DESCRIPTION OF THE DRAWINGS

FIG. 2 shows in vitro adenosine release from silk-based polymers (0 ng, 40 ng, 200 ng and 1,000 ng target implants) in two different scales (A, B). Standard deviations are omitted on the graphs, as they would appear only as background (see text and Table 2 for standard deviation data).

FIG. 8 shows the influence on epileptogenesis by adenosine releasing polymers.

FIG. 11 is a micrograph allowing the characterization of implants before and after implantation. Panels (A) and (B) show examples of Image J degradation analysis (pre-implantation sample #1, Table 1): The total surface area in pixels is measured (Panel A), then the sum of the surface areas of all the pores is measured (Panel B). The percentage porosity is calculated by taking the ratio of pore surface area over total implant area. Scale bars in images A and B=300 µm. Panel (C) Cresyl violet stain of a representative sagittal rat brain section at four weeks post-implantation. The polymer implant is dark blue and indicated with arrow. Scale is bar=3 mm. Panel (D) Hematoxylin & eosin stain showing the morphology of representative infrahippocampal aqueous-derived adenosine-loaded silk fibroin implant after 4 weeks. Scale bar=300 µm. Solid arrow=remaining scaffold.

DETAILED DESCRIPTION

Figure 1:
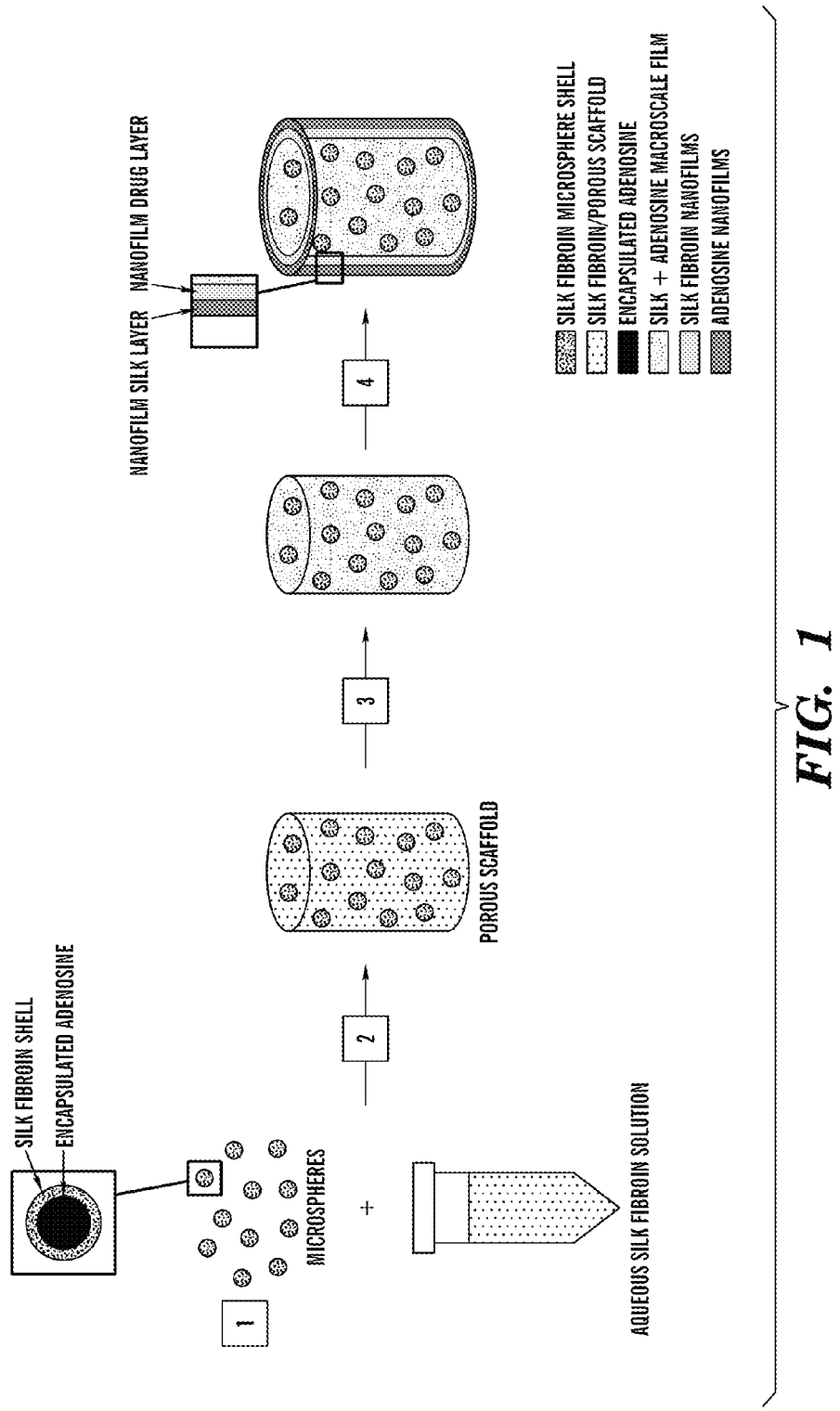
FIG. 1 presents a schematic of implant fabrication showing individual silk-based drug delivery components: (1) Adenosine-encapsulating microspheres are prepared; (2) Microspheres are mixed with silk solution, then porous scaffolds embedded with microspheres are fabricated; (3) Scaffold is soaked in silk+adenosine solution, filling in pores and coating the implant with a macroscale drug-loaded film; and (4) Additional adenosine is loaded with alternating nanofilm deposition.

It should be understood that this invention is not limited to the particular methodology, protocols, and reagents, etc., described herein and as such may vary. The terminology used herein is for the purpose of describing particular embodiments only, and is not intended to limit the scope of the present invention.

As used herein and in the claims, the singular forms "a" "an" and "the" include the plural reference unless the context clearly indicates otherwise. Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described here.

Pharmacoresistant epilepsy continues to remain a major health problem. Despite the availability of an armamentarium of antiepileptic drugs, about 30% of all epilepsies cannot be treated with systemic pharmacotherapy for a variety of reasons including pharmacoresistance and intolerable side effects (Vajda, 14(9) J. Clin. Neurosci. 813-23 (2007)). Moreover, current anti epileptic drugs do little to prevent the development of epilepsy (i.e., epileptogenesis) or to modify the progression of the disease (Löscher et al., 23 Trends Pharmacol. Sci. 113-18 (2002)).

In contrast to systemic delivery, focal drug delivery to the brain generally lacks systemic side effects and holds great promise for epilepsy therapy, which frequently is of focal origin (Nilsen & Cock, 44(2-3) Brain Res. Rev. 141-53 (2004); Pitkanen et al., 48(S2) Epilepsia 13-20 (2007); Kohling, 37(4) Klinische Neurophysiologie 216-24 (2006); Duncan et al., 367(9516) Lancet 1087-100 (2006)). Thus, various cell and gene therapies are currently in development for the treatment of intractable epilepsy (Lösher et al., 31(2) Trends Neurosci 62-73 (2008); Shetty & Hattiangady, 25(10) Stem Cells, 2396-407 (2007); Raedt et al., 16(7) Seizure-Eur. J. Epilepsy 565-78 (2007); Noe et al., 28(2) Peptides, 377-83 (2007); Boison, 5(2) Current Neuropharmacol. 115-25 (2007)).

The recent identification of focal adenosine deficiency as major cause of seizure generation (Li et al., 118(2) J. Clin. Inv. 571-82 (2008); Boison, 84 Prog. Neurobiol. 249-62 (2008)), provides a neurochemical rationale for focal adenosine augmentation therapies (AATs). Focal AATs can be accomplished by implanting adenosine releasing devices or cells into the vicinity of an epileptogenic focus (Boison, 4(1) Neurodegener. Dis. 28-33 (2007a)). The proof-of-principle for the therapeutic efficacy of AATs has been established in animal models of induced or spontaneous seizures (Li et al., 2008; Li et al., 130(5) Brain 1276-88 (2007b); Huber et al., 98(13) P.N.A.S. USA 7611-16 (2001); Boison et al., 160(1) Exp. Neurol. 164-74 (1999). These studies demonstrate that focal AATs can suppress seizures (Huber et al., 2001; Boison, et al., 1999), but might also be capable of retarding or preventing the progression of epileptogenesis (Li et al., 2008; Li et al., 2007). In addition, focal AATs are devoid of systemic and sedative side effects (Güttinger et al., 193 Exp. Neurol. 53-64 (2005)), and augmentation of the adenosine response is effective in suppressing experimental seizures that were refractory to standard antiepileptic drugs (Gouder et al., 44(7) Epilepsia 877-85 (2003)).

Adenosine's anticonvulsant properties are largely mediated by activation of adenosine $A_1$ receptors ($A_1Rs$) that mediate most of the protective functions of adenosine (Fredholm et al., 63 Int. Rev. Neurobiol. 191-270 (2005a); Fredholm et al., 45 Ann. Rev. Phramacol. Toxicol. 385-412 (2005b)). Most importantly, $A_1Rs$ prevent the spread and generalization of seizures, and limit seizure- or injury-induced cell death (Fedele et al. 200 Exp. Neurol. 184-90 (2006); Kochanek et al., 26 J. Cereb. Blood Flow Metab. 565-75 (2006)). Thus, $A_1Rs$ constitute an important target for antiepileptic therapy; in fact $A_1R$ activation prevented seizures in an animal model that was resistant to conventional antiepileptic drugs (Gouder et al., 2003).

Additionally, dysfunction of adenosine-based mechanisms in epilepsy, in particular focal adenosine-deficiency due to upregulation of the astrocyte-based adenosine-removing enzyme adenosine kinase (ADK), have been identified as trigger for ictogenesis (Boison, 84 Prog. Neurobiol. 249-62 (2008b); Li et al., 3 Neuton Glia Bio. 353-66 (2007a); Li et al., 2008). Thus, the astrocyte-specific enzyme ADK has been identified as a molecular link between astrogliosis—a pathological hallmark of the epileptic brain—and neuronal dysfunction in epilepsy (Boison, 3 Future Neurobio. 221-24 (2008a)). Therefore, AATs constitute a rational therapeutic approach to prevent seizures by restoring the adenosinergic equilibrium. Cell transplantation studies suggest that AATs might combine anti-ictogenic with anti-epileptogenic properties (Li et al., 2007b; Li et al., 2008), however with cell-based treatment approaches it was not possible to dissect partly overlapping anti-epileptogenic from anti-ictogenic effects of adenosine, because anti-ictogenesis of cell-based adenosine might have masked anti-epileptogenesis.

Despite AATs potential, problems remain in bringing this approach to the patient population. For example, systemic activation of $A_1Rs$ is of limited therapeutic interest, due to severe cardiovascular and sedative side effects (Dunwiddie & Masino, 24 Ann. Rev. Neurosci. 184-90 (2001)). And although AATs hold great promise for the therapy of refractory focal epilepsies, experimental AATs used previously are not suitable for clinical development due to the use of animal cells (Boison et al., 2007a) or the very short-term duration of therapeutic effect in some of the approaches (Güttinger et al., 2005; Güttinger et al., 46(8) Epilepsia, 1-8 (2005)). Further clinical development of AATs requires the slow and sustained release of adenosine from safe and biocompatible brain implants. Although cell and gene therapies for epilepsy might be considered in the future, the most direct and safest route for the development of AATs may involve biocompatible polymer-based brain implants for the sustained delivery of adenosine.

The embodiments presented herein make use of a novel silk-based time-limited delivery system for adenosine (Wilz et al., 29 Biomats. 3609-16 (2008)), to study anti-ictogenic and anti-epileptogenic effects of focal AAT without any confounds that might be caused by cell-based brain implants. Silk fibroin is a novel biologically derived protein polymer particularly well suited to small molecule drug delivery due to its biocompatibility (Altman et al., 24(3) Biomats. 401-16 (2003)), and relatively slow, controllable biodegradation (Horan et al., 26(17) Biomats. 3385-93 (2005); Wang et al., 29 Biomats. 3415-28 (2008)). Silk can also be processed under aqueous and ambient conditions (Jin & Kaplan, 424 Nature 1057-61 (2003); Li et al., 27(16) Biomats. 3115-24 (2006)), into a diverse range of material formats (Hofmann et al., J. Control Release, 219-27 (2006); Sofia et al., J. Biomed. Mater. Res. 139-48 (2001); Wang et al., 21 Langmuir 11335-41 (2005); Wang et al., 28 Biomats. 4161-69 (2007a)). As used herein, the term "silk fibroin" includes silkworm fibroin and insect or spider silk protein (Lucas et al., 13 Adv. Protein Chem 107-242 (1958)). Fibroin may be obtained from a solution containing a dissolved silkworm silk or spider silk. The silkworm silk protein is obtained, for example, from *Bombyx mori*, and the spider silk is obtained from *Nephila clavipes*. Alternatively, suitable silk proteins can be genetically engineered silk, such as expressed in bacteria, yeast, mammalian cells, transgenic animals or transgenic plants. See, e.g., WO/2008/118133; WO 97/08315; U.S. Pat. No. 5,245,012.

A diverse range of material formats can be generated from silk fibroin, presenting several options to deliver small molecules using silk protein matrix systems. Additional control of drug release from silk biomaterials can be achieved via regulation of β-sheet content (Hofmann et al., 2006) and integration of multiple carrier formats into one implant (Wilt et al., 2008). Silk has been explored as a vehicle for drug delivery in the form of drug entrapping films (Hofmann et al., 111(1-2) J. Control Release 219-27 (2006)), as drug encapsulating microspheres, and via silk and drug nanofilm deposition or coatings (Wang et al., 2007a; Wang et al., 21(24) Langmuir 11335-41 (2005)). Peptides and proteins also have previously been chemically coupled to silk fibroin using carbodiimide chemistry (Sofia et al., 54(1) J. Biomed. Mater Res. 139-48 (2001); Karageorgiou et al., 71(3) J. Biomed. Mater. Res. A 528-37 (2004)). Further, the frequent use of silk sutures in brain and nerve tissue confirms the feasibility of implantation of silk biomaterials in the brain. For example, the relative safety and efficacy of silk sutures for arteriovenous malformation (AVM) and preoperative endovascular embolization has been demonstrated (Dehdashti et al., 11(5) Neurosurg Focus e6 (2001); Schmutz et al., 18(7) AJNR Am. J. Neuroradiol. 1233-37 (1997). Combining different time points of polymer implantation with different kindling paradigms allowed investigation of anti-ictogenic and anti-epileptogenic effects via silk-based adenosine delivery.

As noted above, the versatility in manipulation of silk protein structure and morphology suggests novel delivery options potentially applicable to adenosine delivery. Because each form of silk has its own release profile that can be modulated via processing conditions, the level of control of small molecule drug release can be enhanced by integration of multiple carrier formats into one device or system, such as combinations of ultra-thin coatings, microspheres, and microscale silk films. The system at hand provides for several strategies for a scaled, hierarchically structured protein material delivery approach to orchestrate control of adenosine delivery. The therapeutic potential of these novel AAT devices was validated in the rat kindling model, in which progressive seizure development was studied and quantified as a function of different rates of adenosine release.

In seeking therapeutic alternatives for patients suffering from pharmacoresistant epilepsy, several novel approaches have been developed and tested. These include electrical and magnetic stimulation (Wyckhuys et al., 48(8) Epilepsia 1543-50 (2007); Sun et al., 5(1). Neurotherapeutics, 68-74 (2008); Milby et al., 5(1) Neurotherapeutics 75-85 (2008); Liebetanz et al., 47(7) Epilepsia 1216-24(2006)); focal cooling (Yang et al., 23(3) Neurobiol. Dis. 637-43 (2006)); cell therapies (Loseher et al., 2008; Shetty & Hattiangady, 2007; Thompson, 133(4) Neurosci. 1029-37 (2005); Carpentino et al., 86(3) J. Neurosci. Res. 512-24 (2008)); gene therapies (Vezzani A. 7(12) Expert Rev. Neurother. 1685-92 (2007); Foti et al., 14(21) Gene Ther. 1534-36 (2007); McCown, 14(1). Mol Ther. 63-68 (2006); Raol et al., 26(44) J. Neurosci. 11342-46 (2006)); and ketogenic diet (Masino & Geiger, Trends Neurosci. 2008 in press; Stainman et al., 16(7) Seizure, 615-19 (2007)). Hence, embodiments of the present invention include methods of treating epilepsy, including otherwise pharmacoresistant epilepsy.

A neurochemical rationale for focal AATs has been discussed, and some of the alternative therapeutic approaches are based on adenosine augmentation: adenosine is liberated as a consequence of deep-brain stimulation (Bekar et al., 14(1) Nature Med. 75-80 (2008)), and may be involved in the therapeutic effects of the ketogenic diet (Masino & Geiger, 2008). Thus, focal AATs hold great promise for the treatment of pharmacoresistant partial epilepsy. The therapeutic rationale outlined above prompted the development of a novel AAT, compatible with future clinical application. The approach presented herein combines two FDA-approved materials—silk and adenosine—to develop a biocompatible brain implant for the focal delivery of adenosine.

The in vitro results presented herein suggest that combined, hierarchically designed silk protein devices can be generated to achieve controllable delivery rates of adenosine. All implants continued to release adenosine for at least fourteen days, with average release rates close to target release rates. The average release rates were slightly lower than their target rates, likely the result of implants releasing less than the entire drug load within fourteen days. All implants had high initial release rates, but these rates decreased over fourteen days. This may be the result of the initial "burst" release that is characteristic of many delivery systems, but there are several potential strategies to delay burst and prolong release and achieve near zero order kinetics.

In studies, coatings of the silk microspheres (Wang et al., 2007a); and chemical coupling to the silk (Trayer et al., 139(3) Biochem. J. 609-23 (1974)), are explored as strategies to gain further control of the process. Release experiments suggest that increasing the number of silk capping layers, the crystallinity of the silk, and increasing the nanofilm thickness can slow the rate of drug release. Research correlating the fundamental relationships between material features (e.g., processing conditions, crystallinity, layer thickness) to the release kinetics, enhances predictive models and greater control of drug release rates.

The in vivo results presented herein demonstrate that focal adenosine release from silk-based polymers is effective in retarding kindling epileptogenesis in a dose-dependant manner. This unique approach combined polymers designed to release specified target doses (0 ng, 40 ng, 200 ng, and 1,000 ng adenosine per day) for a limited fourteen day-period with a kindling epileptogenesis paradigm extended to twenty days after polymer implantation to document kindling progression after expiration of the active polymers. In particular, the reciprocal relation of progressive decline in adenosine release with progressive increase in kindling development allowed delineation of dose-response relationships.

Figure 4A:
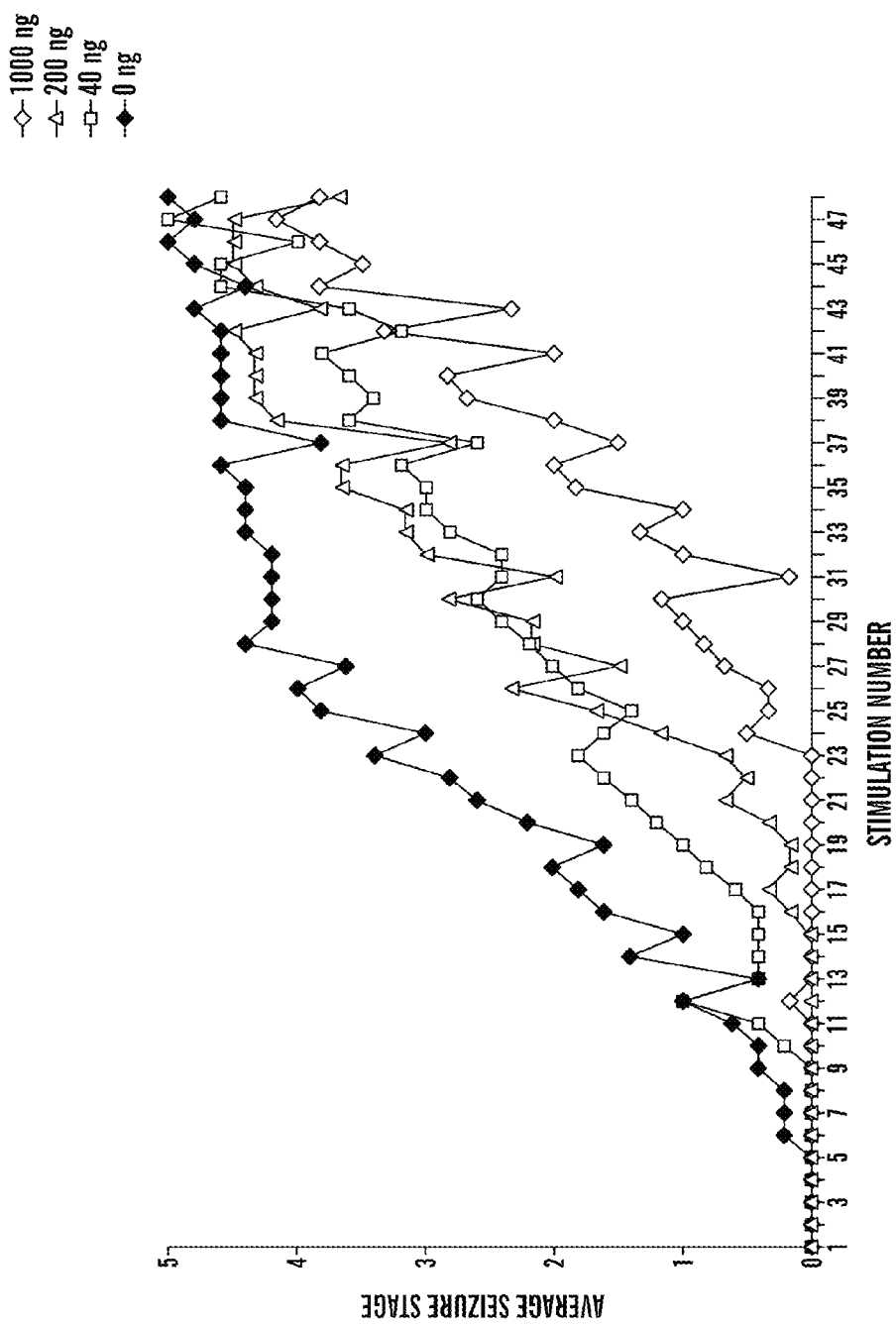
FIG. 4 shows the retardation of kindling after infrahippocampal implantation of adenosine releasing polymers. Four days after infrahippocampal implantation of silk-based polymers with daily target release rates for adenosine of 0 ng (N=5, top line, circles, far-left bar each set), 40 ng (N=5, 2nd line from top, dark squares, 2nd line bar from right each set), 200 ng (N=6, triangles, 2nd bar from left each set), or 1000 ng (N=6, lowest line, diamonds, far left bar each set) kindling stimulations were delivered at a rate of 6 stimulations per day (=session), with session 1 to 8 corresponding to days 4, 6, 8, 11, 13, 15, 18 and 20 following implantation. Panel (A) Seizure stages averaged across animals from each group for each individual stimulation. Kindling curves are shifted to the right with increasing doses of adenosine. Note that recipients of a target dose of 1000 ng adenosine per day were completely protected from any seizures during the first 23 stimulations. Panel (B) Averaged seizure response per session (N=6 stimulations) of the same animals depicted in Panel (A). Note the dose response relationship at session 8. Errors are given as ±SD. Data were analyzed by ANOVA, * $P<0.05$,  $P<0.01$, * $P<0.001$, treatment groups compared to control (0 ng).

This unique adenosine delivery approach allowed the following conclusions, which go beyond results obtained from previous AATs:

(i) Effective dose assessment: The first signs of kindling development (e.g., behavioral seizure scores) typically appear with a delay of one session comprised of six stimulations. Thus, recipients of control implants display first signs of kindling during session 2 (FIG. 4); this implies that kindling epileptogenesis is initiated in the session (i.e., at the relevant dose of adenosine released at that time) preceding the first signs of kindling. Consequently, first signs of kindling appear with a dose dependent delay of about one session in the control group (stimulation #6), two sessions in the 40 ng group (stimulation #10), three sessions in the 200 ng group (stimulation #16), and four sessions in the 1000 ng group (stimulation #24) (FIG. 4A).

This close dose-dependency is also reflected in the average number of stimulations needed to elicit the first stage 1 or stage 2 seizure (FIG. 4) and suggests a linear dose-response relation. Because experiments were designed to prolong kindling after cessation of adenosine release from the polymers, parallel in vitro adenosine release data (Table 3) allowed the determination of the minimal effective dose needed to delay the onset of kindling. This becomes most evident in recipients of a target dose of 1000 ng adenosine per day. These animals continued to be protected from any seizure activity during the first 23 stimulations (i.e., during session 1 to 4) (FIG. 4). First seizures occurred during session 5; taking in consideration the one-session-delay of detecting behavioral seizures, showed that kindling epileptogenesis was initiated during session 4, corresponding to day eleven after polymer implantation. At that time the polymers released approximately 200 ng adenosine per day (Table 3).

Similar calculations performed in recipients of target doses of 40 ng and 200 ng adenosine per day indicated that kindling epileptogenesis was initiated as soon as daily release rates of adenosine fell below 50 ng to 100 ng adenosine (FIG. 4, Table 3). These calculations allow the estimation of the minimal effective dose to be in the range of 50 ng to 200 ng adenosine per day. These data are in agreement with previous cell transplantation experiments, in which adenosine release rates of about 20 ng to 40 ng adenosine released from $10^5$ cells was sufficient to suppress kindled seizures (Huber et al., 2001; Güttinger et al., 2005). Note that high doses of adenosine (>2000 ng adenosine per day) appeared to be well tolerated, without any gross behavioral changes of the animals.

(ii) Possible antiepileptogenic effect: Kindling acquisition occurs with a dose-dependent delay but at the same kindling rate (i.e., progression in seizure severity). This observation suggests that implant-derived adenosine might prevent epileptogenesis. The unique experimental design presented herein, limiting adenosine release to fourteen days (corresponding to session 1 to 5), but extending kindling to twenty days (corresponding to session 8) allowed resuming of kindling after expiration of the polymers. Reduced seizure stages (FIG. 4) combined with the presence but reduced duration of ADDs (FIG. 7) in recipients of adenosine releasing implants during the early stages of kindling could have two alternative explanations: suppression of seizures, however seizure suppression may mask ongoing epileptogenesis; or prevention of epileptogenesis. In the first case, if seizures were simply suppressed by graft-derived adenosine and epileptogenesis was masked by seizure suppression, cessation of adenosine release from the polymers would imply a sudden, rapid rise in seizure severity. This is clearly not the case, however, as shown in FIG. 4. Instead, the rate of kindling acquisition was not changed in recipients of adenosine releasing polymers. Thus, kindling development in recipients of a 1,000 ng per day target dose proceeded at the same rate as kindling development in control animals (FIG. 4), but with a delay in kindling onset. These data suggest that focal polymer-based delivery of adenosine might prevent epileptogenesis. It is important to note that afterdischarges that are considered as the "epileptogenic" stimulus are not suppressed by implant-derived adenosine. The interpretation of these data is consistent with attributing antiepileptogenic effects to increased brain adenosine.

The present embodiments were designed to carefully assess anti-ictogenic and anti-epileptogenic properties of focal adenosine augmentation in kindled rat brain after implantation of silk-based polymers that release a constant, defined dose of adenosine for a limited time. Based on the dose-response study described herein (see also Wilz et al., 2008) polymers releasing a target dose of 1000 ng adenosine per day were selected for further analysis. Focal adenosine augmentation therapies (AATs) are based on the neurochemical rationale that dysfunction of the adenosine system is a neuropathological hallmark of epilepsy and a contributing factor for seizure generation (Boison, 3 Future Neurol. 221-24 (2008a); Boison, 84 Prog. Neurobiol. 249-62 (2008b); Dulla et al., 48 Neuron. 1011-23 (2005); Li et al., 118 J. Clin. Invest. 571-82 (2008); Rebola et al., 18 Eur. J. Neurosci. 820-28 (2003)).

Remarkably, AAT was effective in suppressing seizures in mice that were refractory to standard antiepileptic drugs such as carbamazepine, valproate, and phenytoin (Gouder et al., 44 Epilepsia 877-85 (2003)). Adenosine exerts its antiepileptic effects largely by activation of pre- and postsynaptic adenosine $A_1$ receptors that are coupled to inhibitory G-proteins, decrease presynaptic glutamate release, stabilize the postsynaptic membrane potential, and inhibit adenylyl cyclase (Fredholm et al., 63 Int'l Rev. Neurobiol. 191-270 (2005a); Fredholm et al., 45 Ann. Rev. Pharma. Toxicol. 385-412 (2005b)). $A_1$ receptor activation not only effectively suppresses seizures (Jacobson & Gao, 5 Nat. Rev. Drug Discov. 247-64 (2006)), but also essentially keeps an epileptogenic focus localized (Fedele et al., 200 Exp. Neurol. 184-90 (2006)). Based on these observations $A_1$ receptor activation might combine anti-ictogenic with anti-epileptogenic effects. Due to peripheral side effects of systemic $A_1$ receptor activation (Güttinger et al., 193 Exp. Neurol. 53-64 (2005)), focal AATs become a necessity.

Focal approaches for epilepsy therapy are generally well-tolerated and devoid of undue side effects (Nilsen & Cock, 44 Brain Res. Rev. 141-53 (2004)), and include cell therapies (Boison, 5 Curr. Neuropharmacol. 115-25 (2007b); Loscher et al., 31 Trends. Neurosci. 62-73 (2008); Raedt et al., Seizure-Eur. J. Epilepsy 565-78 (2007); Shetty & Hattiangady, 25 Stem Cells 2396-407 (2007)), and gene therapies (Foti et al., 14 Gene Ther. 1534-36 (2007); McCown, 4 Expert Op. Biologic. Ther. 1171-76 (2004); Raol et al., 26 J. Neurosci. 11342-46 (2006); Vezzani, 7 Expert Rev. Neurother. 1685-92 (2007)). The present embodiments provide for the therapeutic use of silk-based polymers engineered to release adenosine, as a clinically viable therapeutic alternative to achieve focal AAT with the combined goals of anti-ictogenesis and anti-epileptogenesis.

The present embodiments provide for the anti-ictogenic potential of adenosine delivered via silk biopolymer. The anti-ictogenic properties of adenosine are well established (Boison, 2007a). Thus, direct focal injection of adenosine prevented seizures in rats (Anschel et al., 190 Exp. Neurol. 544-47 (2004)), and intraventricular implants of encapsulated adenosine-releasing cells, provide robust seizure suppression in kindled rats (Boison, 2007a). Rodent-cell based cell-therapy approaches are not acceptable for future therapeutic approaches because they involve xenografting. In addition, cell based approaches may preclude detailed dose response studies. As a first step to develop a novel AAT that is compatible with future clinical applications two FDA approved compounds, silk and adenosine, were combined into one biocompatible, biodegradable focal delivery system for adenosine. Using this novel type of polymers a dose-response study was performed that demonstrated dose-dependent (target release rates of 0, 40, 200, and 1000 ng adenosine per day) retardation of kindling development in rats (Wilz et al., 2008).

A particular example of the present invention provides a formulation in which adenosine-releasing implants can suppress fully kindled seizures and anti-ictogenic and differentiate anti-epileptogenic effect: silk-based polymers that released a constant dose of around 1000 ng adenosine per day from day four to day ten, before gradually declining to non-detectable levels of adenosine (FIG. 3). The polymers were designed to release adenosine for a limited time to specifically assess seizure responses after expiration of adenosine release. The Examples below demonstrate complete suppression of fully kindled seizures during the first ten days of polymer implantation (FIG. 6) in line with the specific release profile of the polymers (FIG. 3). Importantly, seizures begin to recur during expiration of adenosine release from the polymers (from day fourteen to twenty-one). This finding is of importance for two reasons: (i) recurrence of seizures after expiration of adenosine release from the polymers indicates that seizure suppression depends on implant-derived adenosine; (ii) the precise match of therapeutic effectiveness with the release properties of the polymer is a prerequisite for the anti-epileptogenesis studies presented herein.

Several recent studies suggested a novel anti-epileptogenic role of focal AATs: (i) Both, stem cell derived (Li et al., 2007b), as well as silk-polymer based (Wilz et al., 2008) (described herein), infrahippocampal implants designed to augment hippocampal adenosine retarded the progression of kindling epileptogenesis in rats. (ii) In a mouse model of CA3-selective epileptogenesis that includes astrogliosis and upregulation of ADK as pathological hallmarks of epileptogenesis, infrahippocampal stem cell derived adenosine-releasing implants reduced astrogliosis, prevented upregulation of ADK, and the occurrence of spontaneous seizures; in particular, the anti-astrogliotic effect of these cell-based implants can be interpreted as anti-epileptogenic effect.

Thus, a specific embodiment was designed to test possible anti-epileptogenic effects of implant-derived adenosine. To achieve this goal engineered silk-based polymers were engineered to release a stable amount of adenosine over a limited time frame (1000 ng adenosine per day for up to ten days). Two independent approaches were designed to demonstrate anti-epileptogenesis by these implants; in both approaches the polymers were implanted prior to the onset of kindling. In one example, implant recipients were kindled every other day from day four to eleven (corresponding to a total of twenty-four stimulations). Compared to control implant recipients, recipients of adenosine-releasing implants were characterized by marked retardation in the expression of kindled seizures (FIG. 6A). At this time point, DPCPX failed to increase seizure scores in adenosine-releasing implant recipients indicating that the lack of higher seizure scores was not due to adenosine-based seizure suppression. These findings demonstrate an anti-epileptogenic effect of the adenosine releasing brain implants. Another approach was designed to initiate kindling during the phase of constant high release of adenosine (1000 ng per day from days four to eight) (FIG. 3), and to resume kindling after a delay period of nine days, a time frame during which adenosine release from the polymers had expired. This experimental paradigm is suited to quantify the degree of antiepileptogenesis (Silver et al., 1991).

Drugs that do not have any anticonvulsant effects (e.g., carbamazepine, Silver et al., 1991) result in matching kindling curves between control and treatment groups, both during and after the drug phase; thus, carbamazepine did not affect kindling development during the drug-phase. Drugs that have partial antiepileptogenic effects (e.g., phenobarbital, Silver et al., 1991) display suppression of kindling development during the drug phase and resume kindling development at the same stage at which kindling was discontinued. In the case of phenobarbital, however, the number of drug-free afterdischarges needed to elicit seizure stages corresponding to the control group was reduced, indicating partial antiepileptogenesis. Drugs that exert complete antiepileptogenic effects (e.g., valproate, Silver et al., 1991) display suppression of kindling development during the drug phase, resume kindling after discontinuation of the drug at the same stage as before discontinuation of the drug, but the numbers of drug-free afterdischarges to elicit corresponding seizures in drug-treated and control animals is the same.

According to these considerations, the data (FIG. 8B) demonstrate almost complete suppression of kindling development during the first 24 kindling stimulations in recipients of adenosine-releasing implants. After the 30th stimulation delivered at day eight, recipients of adenosine-releasing implants were still strongly protected with seizure scores around 1. At the same time, recipients of control implants were completely kindled. When kindling was resumed at day eighteen, adenosine-releasing implant recipients were still protected, and in the absence of implant-derived adenosine gradually developed kindled seizures. The progression of seizure development in these animals was in parallel to kindling development in control animals, however the number of drug-free afterdischarges needed to elicit seizure stages corresponding to those in control animals was reduced. According to McNamara's considerations our findings demonstrate that the transient release of adenosine during the first kindling sessions (day four to day eight) provided partial prevention of epileptogenesis. If lack of seizures during that time were due to adenosine-based seizure suppression (masking epileptogenesis), then animals should have reacted with stage 5 seizures according to the control animals at day eighteen. Note that despite the lack of behavioral seizures, an electrographic afterdischarge was always elicited even in recipients of adenosine releasing implants (FIG. 9), indicating that animals were kindled with supra-threshold stimulations that are expected to deliver an epileptogenesis-relevant trigger.

The beneficial mechanisms how chronic augmentation of brain adenosine, as achieved by the implants described here, might at least partially contribute to the prevention of epileptogenesis need to be distinguished from mechanisms of acute rises in adenosine to micromolar levels (Fredholm et al., 2005a) as a response to injury that are thought to trigger astrogliosis (Boison, 2008b). The mechanistic differences of opposing downstream-effects of chronic implant-based increases in adenosine, versus acute high-level increases in adenosine during brain injury, are being elucidated.

Several mechanisms may be involved: (a) The moderate increase in adenosine levels achieved by brain implants might be insufficient to trigger receptor expression changes on astrocytes and might preferentially activate astrocytic $A_1$ receptors, and thus promote anti-epileptogenic effects via astrocyte modulation; (b) In contrast, acute high levels of adenosine inhibit adenosine kinase (Mimouni et al., 269 J. Biol. Chem. 17820-25 (1994)), thus high levels of adenosine after acute injury may trigger upregulation of adenosine kinase as a compensatory mechanism linked to epileptogenesis (Li et al., 2008); and (c) An acute rise in adenosine to micromolar levels (i.e., as occurs after injury or during prolonged status epilepticus) may lead to changes in astrocytic adenosine receptors, most notably downregulation of $A_1$ receptors involved in regulating astrocyte proliferation; changes in astrocytic adenosine receptors could then trigger astrogliosis as part of the epileptogenic cascade.

Therapeutic potential of biodegradable adenosine-releasing polymers is demonstrated herein. The degradation of the scaffolds demonstrated here (FIG. 11; Table 4) suggests the presence of silk-degrading proteases in rat brain. For example, chymotrypsin has been shown to degrade silk (Li et al., 2003) and a number of chymotrypsin-like proteases have been identified in rat brain. Caldecrin (a chymotrypsin-like protease) was demonstrated to be expressed within the hippocampus of adult rat brain (Tomomura et al., 317 Neurosci. Lett. 17-20 (2002)). Specific proteases involved in the process and modes to regulate the degradation lifetime of this type of implant may be characterized further. The biodegradability of silk-based polymeric implants demonstrated herein constitutes a major advantage for the preventive use of this type of brain implant. Partial anti-epileptogenic effects of adenosine-releasing silk-scaffolds as provided for herein permit the preventive use of such implants in patients of high risk in developing epilepsy, e.g., after traumatic brain injury. Thus, silk-based adenosine-releasing scaffolds could be implanted into a traumatized brain area shortly after the injury, making synergistic use of the neuroprotective (Cunha, 1 Purinergic Signaling 111-34 (2005)), anti-ictogenic, and possible anti-epileptogenic properties of adenosine. Sustained delivery of adenosine might improve the therapeutic outcome in these patients and eventually the polymer would be completely degraded and resorbed without leaving any residues.

Several of the present embodiments provide for adenosine-release during a restricted time window. This specific design of the implant allowed evaluation of possible anti-epileptogenic effects of adenosine and demonstration of seizure suppression in fully kindled rats. The present data, but also those derived from other studies (Li et al., 2007a; Li et al., 2007b; Li et al., 2008; Wilz et al., 2008), suggest at least partial anti-epileptogenic effects of focal AATs. Additional studies, including dose-response studies and the use of different models of epileptogenesis, further address anti-epileptogenic effects of adenosine.

The current embodiments support the design of long-term seizure suppression implants. For long-term seizure suppression, the design of the implants can be modified to allow sustained long-term delivery of adenosine. The 3D porous matrices can be processed to function in vivo from weeks to a year or more depending on the mode of processing (Wang et al., 117 J. Control Release, 360-70 (2007b)). For example, because of its excellent entrapment capability, MeOH-based silk microspheres provide long-term drug delivery (WO/2008/118133). Additionally, the release of adenosine may be controlled by entrapping the adenosine not only in the 3D matrix, but in silk layers surrounding the matrix, via inducing the transition to the β-sheet (e.g., methanol, shear, salts, electric, dehydrating gas flow) and adding layers on this, with each layer entrapping the next dose of adenosine. This layer-by-layer approach produces an onion like structures with selective loading in each layer. Further, the extend of β-sheet induction in each layer may be manipulated to effect burst release and sustained release. Additionally, one or more layers containing no added adenosine (barrier layer) can be deposited on the layers containing the adenosine to control release and/or limit the initial burst. The thickness of each deposited layer may be affected by controlling the concentration of fibroin in the silk fibroin solution, or the pH of the fibrin solution used to form the layer. Layers may be from 1 nm to several μm thick may be produced. Thus the number of layers, the thickness of layers, and induction of β-sheet structure in the layers, and the concentration of adenosine in each layer may be designed to yield a desired release profile (WO 2005/123114; WO 2007/016524).

Another embodiment of the present invention provides for the prevention or treatment of epilepsy in a subject, including a human subject, by implanting a silk fibroin-based adenosine-releasing composition directly into the brain of the subject. The therapeutic dosing and regiment most appropriate for subject treatment will of course vary with the disease or condition to be treated, and according to the subject's hippocampal size and other parameters. The adenosine dose of the implant may be from about 50 ng adenosine per day to about 50 mg adenosine per day, inclusive, such as 25 ng adenosine per day or 250 ng adenosine per day, depending on size of the subject's hippocampus, the size of the epileptic focus, and in implantation site. For example, a lower dose may be required if the implant is placed directly into the epileptic focus; a higher dose may be required if the implant is placed into the ventricular system in the vicinity of the epileptic focus.

The length of time over which adenosine is delivered may be from about one month to over one year, inclusive. For example, short term delivery, e.g., one month following an epileptogenesis-triggering event, such as a traumatic brain injury, may prevent epileptogenesis. Because epilepsy is typically a permanent disease, a therapeutic implant system may be used to provide seizure control during the lifetime of a subject. Thus, an embodiment of the present invention provides for an implant system in which the silk-fibroin adenosine implant delivers adenosine for about one year, after which any expired scaffold is removed and replaced with a fresh implant, which system may be achieved via permanently implanted catheters.

Thus, for example, in the case of traumatic brain injury (TBI) in an adult male, as an direct result of the TBI there will be a cavity or core of dead tissue that can be diagnosed by current imaging technology. This core and its vicinity will eventually scar (within about two weeks) and develop into a focus of seizure activity. This core of the injury, rather than the ventricular system, is the logical site for implantation. The implant may be roughly spherical, with a diameter of about 0.5 cm, releasing between about 1 mg and about 10 mg adenosine per day during a time span of about one month.

For long-term ATT, one surgical approach would be to place an implant into the ventricle that contacts the affected hippocampus. In this embodiment, an implant sized about 1×3×5 mm would fit into that space; if its form could be slightly concave, such that it forms a "layer" of adenosine-releasing implant touching the hippocampus, delivering about 200 ng to about 5 mg adenosine per day. Accordingly, adenosine sustained release formulations are implanted in subjects to reduce or ameliorate symptoms associated with epilepsy. Therapeutic endpoints for the treatment of epilepsy include a reduction of disease parameters such as seizure frequency, seizure severity and EEG abnormalities.

In another embodiment of the invention, the adenosine, silk-based scaffolds can be combined with human mesenchymal stem cells (hMSCs) engineered to release adenosine (U.S. Pat. No. 6,110,902; WO 2007/016524). For example, an RNAi-based lentiviral method to engineer hMSCs for therapeutic adenosine release has been demonstrated (Ren et al., 208 Exp. Neural. 26-37 (2007)). Infrahippocampal implants of these cells reduced acute kainic acid induced brain injury and seizures (id.). Additionally, hMSCs taken from a patient and engineered to release adenosine may be used as autologous brain implants in combination with biodegradable silk-based scaffolds of the present invention. Such MSC-loaded silk scaffolds provide for permanent adenosine therapeutic activity.

In conclusion, the embodiments described herein provide for novel silk-based delivery system for adenosine that fulfills crucial requirements for future clinical application, such as: (i) biocompatibility, (ii) delivery of predetermined doses of adenosine, (iii) safety, (iv) sustained function via slow degradation in vivo, and (v) therapeutic efficacy in a widely used preclinical model (rat kindling model) that has a high predictive value in drug development. Additionally, the present invention defines for the first time a minimally effective doses in the range of 50 ng to 200 ng adenosine per day, and suggests that focal delivery of adenosine might not only have therapeutic value for the suppression of established seizures, but also for the prevention of epileptogenesis.

The invention will now be described further by non-limiting examples.

EXAMPLES

Example 1

Implant Design

Implants designed to deliver the target doses (0 ng, 40 ng, 200 ng, and 1,000 ng per day) were designed based on preliminary experiments to determine drug loading. Implants were also designed to split the target drug load roughly evenly between the three systems chosen for integration in the study, microspheres, macroscale films, and nanofilms. The three variables used to impact the final adenosine dose were: (1) the concentration of microspheres in the silk solution that were formed into water-based, porous scaffolds, (2) the concentration of adenosine in the adenosine plus silk solution that the porous scaffolds were coated with to form the macroscale silk films, and (3) the number of layers of nanofilms deposited on the system. The composition of the implants and the theoretical amounts of adenosine loaded via each technique are listed in Table 1.

TABLE 1

Implant compositions and loading with adenosine. The number of nanofilms includes both a silk nanofilm and the subsequent adenosine nanofilm. Ado = adenosine.

| | Nanofilms | | Microspheres | | Macroscale Film | | Total Ado |
| --- | --- | --- | --- | --- | --- | --- | --- |
| | | | Conc. of | | | | |
| | Number of nanofilms | Total Ado loaded | microspheres in silk solution | Total Ado loaded | Conc. of Ado in silk solution | Total Ado loaded | loaded for entire implant |
| 40 ng/day | 3 | 250 ng | 10 mg/mL | 160 ng | 0.06 mg/mL | 150 ng | 560 ng |
| 200 ng/day | 12 | 1,000 ng | 50 mg/mL | 800 ng | 0.4 mg/mL | 1,000 ng | 2,800 ng |
| 1,000 ng/day | 36 | 3,000 ng | 250 mg/mL | 4,000 ng | 2.8 mg/mL | 7,000 ng | 14,000 ng |

Example 2

Implant Fabrication

The implant fabrication process is represented in FIG. 1. Silk for the study was prepared from Bombyx mori cocoons as previously described (Sofia et al., 2001). Adenosine-containing microspheres were prepared according to the MeOH based protocol described previously (Wang et al., 2007). Briefly, 200 µL of 10 mg/mL adenosine stock solution was mixed with 1 mL of 8% (w/v) silk aqueous solution, which was then added to 200 mg of 1,2-Dioleoyl-sn-Glycero-3-Phosphocholine (DOPC) phospholipid that had been dissolved in 1 mL of chloroform, then dried under $N_2$ to a film on the interior of a glass test tube. The solution is diluted, then repeatedly freeze-thawed, then lyophilized. Later, the microspheres were treated with methanol (MeOH) to remove the lipids and induce β-sheet silk physical crosslinks to stabilize the microsphere structures. Ethanol or sodium chloride may be used instead of is methanol in the fabrications described herein, and these agents also induce β-sheet structure. See WO 2008/118133. Additionally, β-sheet structure induction and annealing of the silk fibroin microspheres (or films, below) may be accomplished by water vapor exposure. See WO 2008/127402.

Water-based porous scaffolds were prepared as previously described (Kim et al., 26(15) Biomats. 2775-85 (2005)), using the mixture of microspheres and silk solution to imbed the microspheres in the final porous scaffold. Briefly, 4 g of 500 µm-600 µm granular NaCl were added to 2 mL of 6% (w/v) silk solution mixed with microspheres in a plastic container and incubated at room temperature for over 24 hr. The scaffolds were then washed for 24 hr to leach out the sodium chloride. To obtain the desired implant geometry (0.6 mm-0.7 mm diameter, 3 mm length), scaffolds were punched out with a 1 mm Miltex biopsy punch and then trimmed with a razor on either end. The porous scaffolds were next coated with macroscale drug-loaded silk films comparable to the films described previously (Hofmann et al., 111 J. Control Release 219-227 (2006)). Implants were soaked in a mixed silk-and-drug solution for 2 min, then incubated at 60° C. for 15 min-20 min, then washed in a 90% MeOH solution.

Finally, nanofilm coatings were applied using a previously described protocol (Wang et al., 21(24) Langmuir, 11335-41 (2005)), but modified to accommodate coating of a 3-dimensional (3D) porous scaffold. Scaffolds were first dipped in a 2 mg/mL silk fibroin solution for 2 min, and then washed in 90:10 (v/v) MeOH/water solution for 1 min. Following the methanol wash, the scaffolds were dried at 60° C. for 15 min. The dried scaffolds were then dipped in a 1 mg/mL adenosine solution for 2 min and dried at 60° C. for another 15 min. These steps were repeated until the desired number of layers was achieved, ending with a silk layer. After drug loading, all implants were coated with three capping layers (three subsequent silk dips) to delay burst.

Additional means and methods for designing and manufacturing silk adenosine-delivering implants may be made with reference to this specification and, e.g., U.S. Patent Application Publication No. 20080085272; WO 2007/016524; WO/2008/118133.

Example 3

In Vitro Release Studies

For each target dose (40 ng, 200 ng, and 1,000 ng) three implants were characterized for release kinetics in vitro (N=3). To evaluate release profiles, implants were immersed in 1 mL of Dulbecco's phosphate buffer, pH 7.2 (PBS) at 37° C. At pre-set time points (1, 2, 3, 4, 6, 10 and 14 days) the PBS was removed and replaced.

Adenosine content in the PBS samples removed from the system was measured using a modified fluorescence assay as previously described (Wojcik & Neff 39 J. Neurochem. 280-82 (1982)). The collected PBS sample was transferred to a 1.5 mL Eppendorf tube and chloroacetaldehyde was added to a final concentration of 220 μM chloroacetaldehyde. These tubes were capped and boiled for 20 min. Boiling of mixed adenosine and chloroacetaldehyde yields the fluorescent derivative 1,N6-ethenoadenosine. The fluorescence of the sample was measured with a plate reader (excitation=310 nm, emission=410 nm (Rosenfeld & Taylor, 259(19) J. Biol. Chem. 11920-29 (1984). For each device at each time point, three fluorescence readings were taken and averaged.

Example 4

Animals and Surgery

All animal procedures were conducted in a facility accredited by the Association for Assessment and Accreditation of Laboratory Animal Care in accordance with protocols approved by the Institutional Animal Care and Use Committee and the principles outlined in the NIH Guide for the Care and Use of Laboratory Animals. Adult male Sprague-Dawley rats were used at a body weight of 280 g to 300 g. All rats were acclimatized for one week before being used in the experiments. The rats were housed under a 12-hour light/dark cycle (lights on from 8:00 A.M) with food and water provided ad libitum.

Anesthesia was induced with 3% isoflurane, 67% $N_2O$, 30% $O_2$ and maintained with 1.5% isoflurane, 68.5% $N_2O$, 30% $O_2$, while rats (N=22) were placed in a Kopf stereotactic frame. First, polymers with a target release rate of 0 ng, 40 ng, 200 ng, and 1000 ng adenosine per day (N=5-6 per dose) were implanted using a stereotactic implantation device (internal diameter 0.7 mm, external diameter 1 mm) as described (Boison 43(8) Epilepsia, 788-96 (2002). The polymer-loaded device was stereotactically inserted into the brain using a drill hole above the left hemisphere 2 mm rostral to bregma and 1.6 mm lateral to the midline. Using this drill hole the loaded device was inserted into the brain using an angle of 45° from vertical and an angle of 45° from midline. Thus, a diagonal injection tract was created aiming at a coordinate of 5.5 mm caudal to bregma, 5.5 mm to the right of the midline and 7.5 mm below the dura. Upon reaching the target site the 3 mm long polymer was released and deposited within the infrahippocampal cleft by slowly retracting the outer tube of the device. Finally, the device was fully retracted as described previously (id). Thus, the implanted polymers were deposited within a formed cavity of 3 mm length within the right infra-hippocampal cleft and adjacent to the electrode implantation site.

The diagonal implantation approach pursued here and previously (Li et al., 2007; Li et al., 2008), is characterized by a number of important advantages: (i) Coverage of 3 mm of the dorso-ventral extent of the hippocampus by placement of the implants into the infra-hippocampal fissure; (ii) Minimization of damage to the ipsilateral hippocampus; (iii) Compatibility with the electrode-containing head-set of the animals. Next, a bipolar, coated, stainless steel electrode (0.20 mm in diameter, Plastics One, Roanoke, Va.) was implanted into the right hippocampus and fixed with a head-set of dental acrylate. Coordinates for the hippocampal electrodes were (tooth bar at 0): 5.5 mm caudal to bregma, 5.5 mm lateral to midline, and 7.5 mm ventral to dura.

Example 5

Kindling

Four days after surgery, the animals were stimulated unilaterally six times every second or third day with a Grass S-88 stimulator (1-ms square-wave pulses of 5V at 50-Hz frequency for 10 sec; 30 min-interval between stimulations). Behavioral seizures were scored according to the scale of Racine (3(2) Neurosurg. 234-52 (1978)). Each animal received a total of 48 stimulations, which was equivalent to eight test days spread out between day 4 and day 20 following polymer implantation. The electroencephalogram (EEG) was recorded for periods of 1 min before and 5 min after application of each stimulating pulse using a Nervus EEG monitoring system.

Example 6

Histology

After completion of the experiments the rats were transcardially perfused with 4% paraformaldehyde in phosphate buffer (0.15 M, pH 7.4). Brains were then post fixed in the same fixative for 6 hr and cryoprotected in 10% DMSO in PBS (v/v) before being cut into a total of seventy-two coronal sections (40 μm thickness) covering the full extent of the lateral hippocampus (3.5 mm to 6.5 mm caudal to bregma). To characterize gross anatomy of the brain in particular in the implant region, and to verify the precise location of the kindling electrodes, a Cresyl violet stain was performed on every sixth section.

Example 7

Statistics

In the in vitro studies, standard deviations were calculated for the three repetitions per dose. The values for each of the three repetition implants loaded with the same dose were obtained by averaging three fluorescence readings per implant. Standard deviations are listed in Table 2.

TABLE 2

Average adenosine release (Ado = adenosine, all values in ng)

| | Target: 40 ng | | Target: 200 ng | | Target: 1,000 ng | |
|---|---|---|---|---|---|---|
| Days | Ado Release | Cumulative Release | Ado Release | Cumulative Release | Ado Release | Cumulative Release |
| 1 | 134.4 (±13.8) | 134.4 | 679 (±25.0) | 679 | 3137 (±86.5) | 3137 |
| 2 | 89.0 (±10.5) | 223.4 | 513.1 (±21.1) | 1192.1 | 2865.2 (±55.8) | 6002.2 |
| 3 | 33.9 (±9.9) | 257.3 | 202.3 (±22.3) | 1394.4 | 984.6 (±79.7) | 6986.8 |
| 4 | 66.3 (±4.4) | 323.6 | 330.9 (±18.4) | 1725.3 | 2042.7 (±61.2) | 9029.5 |
| 6 | 42.7 (±3.4) | 366.3 | 208.4 (±15.4) | 1933.7 | 853.7 (±44.0) | 9883.2 |
| 10 | 62.4 (±4.5) | 428.7 | 281.3 (±15.8) | 2215.0 | 914.8 (±50.6) | 10,798 |
| 14 | 38.7 (±10.8) | 467.4 | 172.3 (±22.3) | 2387.3 | 667.3 (±45.4) | 11,465.3 |

In vivo seizure data are based on N=5 rats for recipients of control polymers (0 ng adenosine) and for recipients of the 40 ng adenosine/day polymers, and N=6 for recipients of the 200 ng and 1,000 ng adenosine/day polymers. Individual seizure scores and afterdischarge durations were pooled and averaged for each of the eight test days in each experimental group. Errors are given as ±SD and data were analyzed using one-way ANOVA with Student-Newman-Keuls Test. * $P<0.05$,  $P<0.01$, * $P<0.001$.

Example 8

Adenosine Release Kinetics in Vitro

The average release of adenosine from the implants at each time point and the cumulative release over 14 days are summarized in Table 2, above. Over fourteen days, the 8 ng target implant released a total of 100.9 ng (average release rate=7.2 ng/day), the 40 ng target implant released 467.4 ng (average release rate=33.4 ng/day), the 200 ng target implant released 2387.3 ng (average release rate=170.5 ng/day) and the 1,000 ng target implant released 11,465.3 ng (average release rate=819 ng/day). Release rates for each time point are summarized in Table 3. The cumulative release curves are displayed graphically in FIG. 2.

TABLE 3

Release rates of adenosine from implants (ng/day)

| Days | Target: 40 ng | Target: 200 ng | Target: 1,000 ng |
|---|---|---|---|
| 1 | 134.4 | 679 | 3137.0 |
| 2 | 89.0 | 513.1 | 2865.2 |
| 3 | 33.9 | 202.3 | 984.6 |
| 4 | 66.3 | 330.9 | 2042.7 |
| 6 | 21.4 | 104.2 | 426.9 |
| 10 | 15.6 | 70.3 | 228.7 |
| 14 | 9.7 | 43.1 | 166.8 |
| Average | 33.4 | 170.5 | 819.0 |

Example 8

Dose Dependent Suppression of Kindling Epileptogenesis by Infrahippocampal Adenosine Releasing Implants Infrahippocampal implantation of silk-based polymers with different target release rates of adenosine ranging from 40 ng to 1000 ng adenosine/day should suppress kindling epileptogenesis in a dose-dependent way. To test this hypothesis, four groups of rats received infrahippocampal implants with target release rates of 0 ng (control, N=5), 40 ng (N=5), 200 ng (N=6), and 1000 ng (N=6) adenosine per day. These target doses were based on previous dose assessments suggesting an effective dose to be in the range of 200 ng adenosine released/day (Huber et al., 2001; Boison et al., 1999). Four days after polymer implantation hippocampal kindling was initiated with each rat receiving a total of eight kindling sessions every second or third day, with each session comprised of six stimulations delivered every 30 min. Thus, during a time span ranging from four days to twenty days after stimulation, each rat received a total of 48 stimulations (FIG. 4A).

Figure 4B:
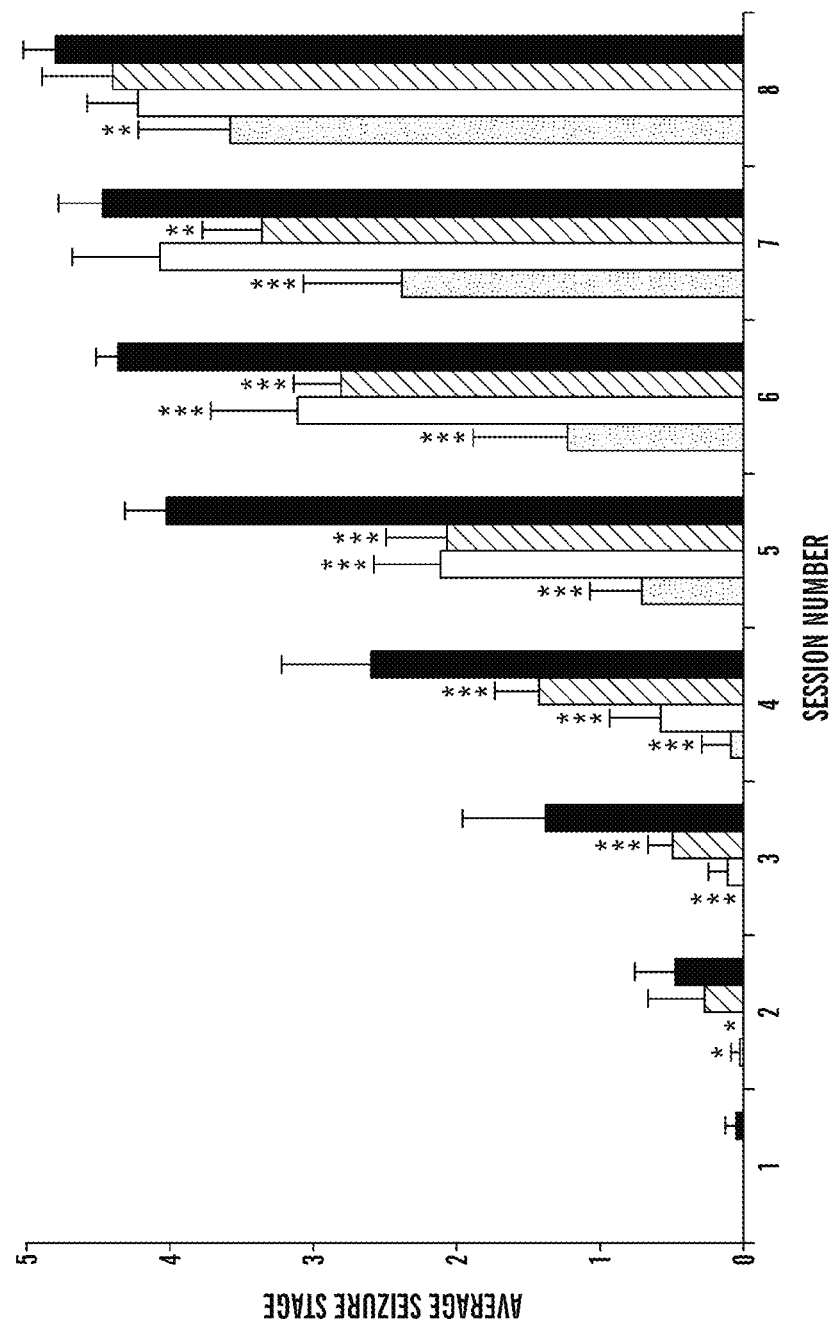
Figure 5:
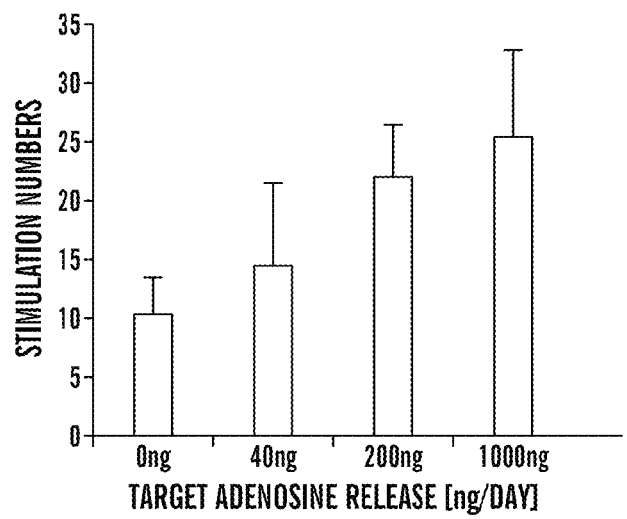
FIG. 5 shows the number of kindling stimulations needed to elicit partial stage 1 or stage 2 seizures. Data were averaged from seizure score tables from the animals of FIG. 4. Errors are given as ±SD.

Seizure scores were determined after each stimulation according to the scale of Racine (1978). Stages 1 to 3 correspond to partial seizures of progressing intensity, whereas stage 4 and stage 5 represent generalized seizures with tonic and clonic components. Compared to control (0 ng adenosine) kindling development in recipients of target doses of 40 ng, 200 ng, and 1000 ng was initially delayed in a dose-dependent relation during the first 24 sessions or until the end of session four that corresponds to eleven days after polymer implantation. Most notably, during this time recipients of polymers releasing a target dose of 1000 ng/day were completely protected from any seizure activity (FIGS. 4A, 4B). This dose-dependent therapeutic effect was also reflected by the number of stimulations, needed to elicit the first partial (stage 1 or stage 2) seizure (FIG. 5). Although in recipients of control implants partial seizures first occurred during session 2 (i.e., around stimulation 10), the first emergence of partial seizures was markedly delayed with increasing doses of released adenosine with recipients of a target dose of 1000 ng adenosine/day needing 2.5 times as many stimulations to reach the same kindling state as the control group (FIG. 5).

From stimulation 25 onwards (i.e., session 5 at day thirteen after implantation) the therapeutic effects of the implants declined (FIG. 4), which is consistent with the reduced rate of adenosine release from the polymers (Table 3). Recipients of control implants reached their kindling criteria (generalized stage 4/5 seizures) from session 5 onwards, but recipients of adenosine releasing polymers showed a delay in the acquisition of generalized seizure responses (FIG. 4). Interestingly, the kindling rates (i.e., the progressive increase in seizure stages with time) were similar in recipients of target doses of 0 ng, 200 ng, and 1000 ng adenosine/day, with a dose dependent delay in kindling onset, indicating polymer-based adenosine-release suppressed kindling. Most importantly, recipients of a target dose of 1000 ng adenosine/day showed a delay of kindling acquisition of about three sessions or one week, indicating that doses of around 400 ng adenosine/day (Table 3) are sufficient to suppress kindling.

Example 9

Figure 7A:
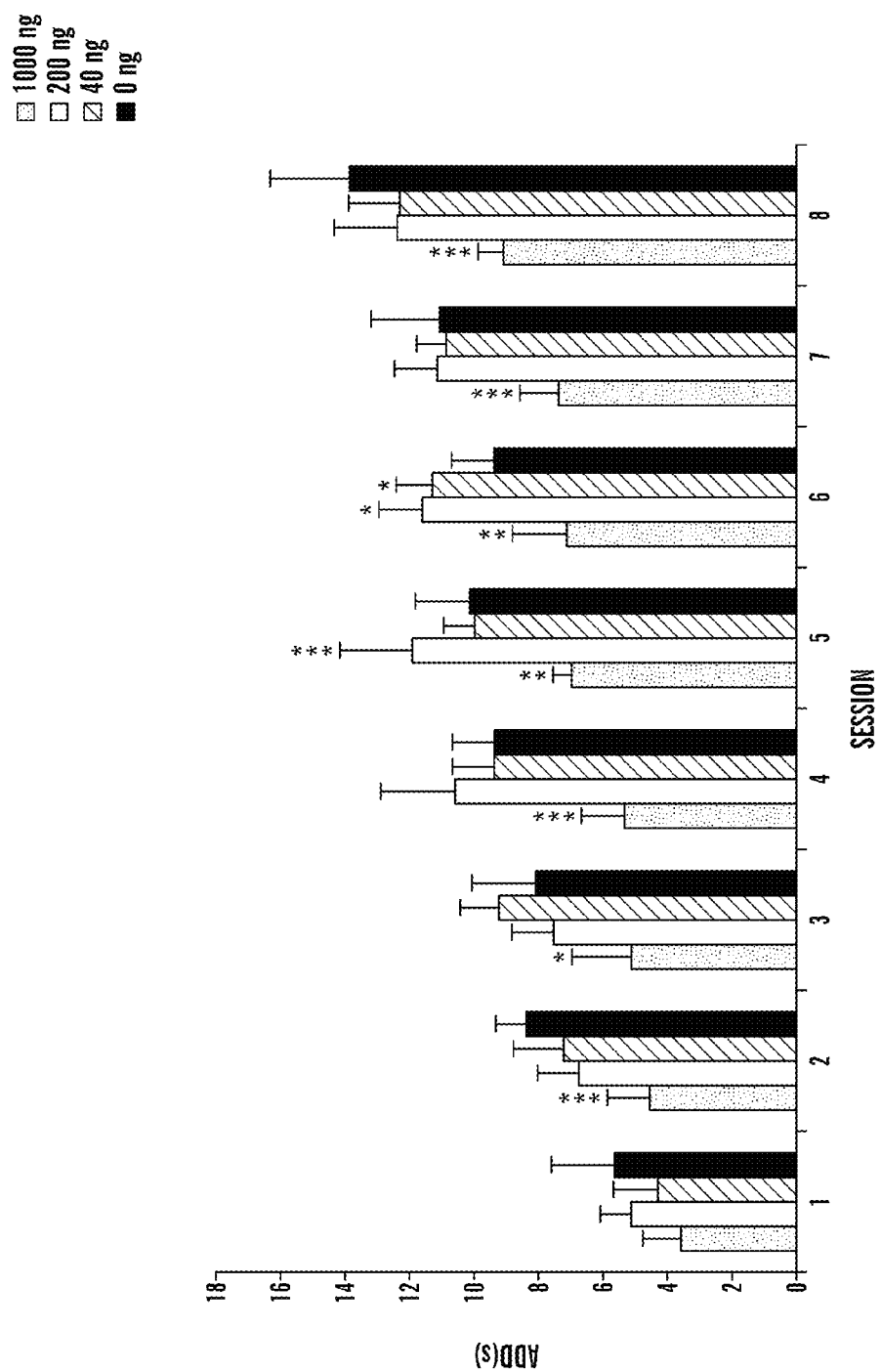
FIG. 7 depicts the average duration of after-discharge in EEG recordings during kindling acquisition. Panel (A) shows the after-discharge duration (ADD) as determined after each kindling-stimulation by analyzing the respective EEG recordings. ADDs were averaged for each session (n=6 stimulations) and treatment type: implants releasing target doses of 0 ng (far right bar each set, N=5), 40 ng (penultimate right bar each set, N=5), 200 ng (penultimate left bar, N=6), or 1000 ng (far left bar each set, N=6) adenosine per day. Errors are given as ±SD. Data were analyzed by ANOVA: * $P<0.05$,  $P<0.01$, * $P<0.001$, adenosine releasing polymer implants versus control (0 ng adenosine). Panel (B) is a representative EEG recording at session 5 from an animal with a control implant. Panel (C) shows a representative EEG recording at session 5 from an animal with a target release dose of 1,000 ng adenosine/day.
Figure 7B:
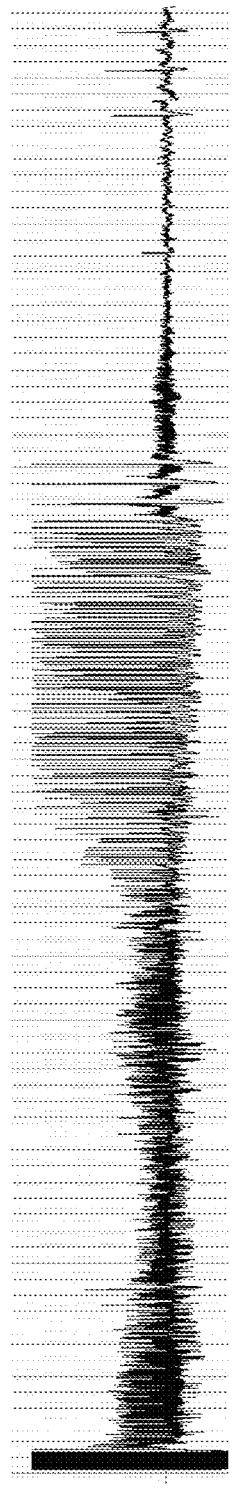
Figure 7C:
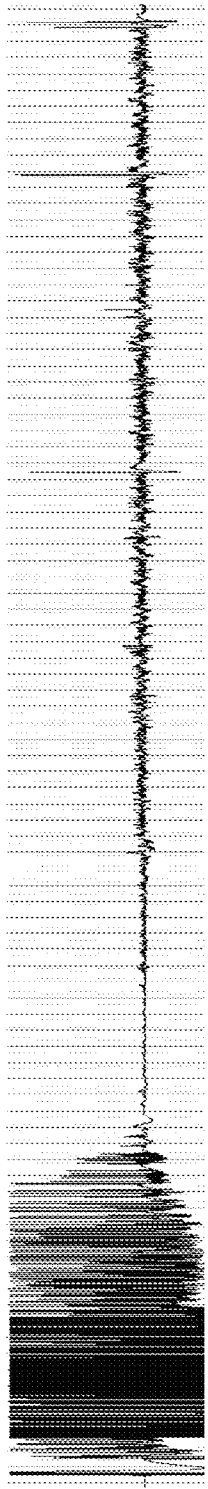

Infrahippocampal Adenosine Releasing Implants Reduce after Discharge Duration in EEG Recordings The therapeutic effect of the adenosine-releasing infrahippocampal implants was further quantified by determination of the duration of electroencephalographic afterdischarges (ADD) elicited by each test stimulus during the kindling acquisition phase (FIG. 7).

Figure 10:
FIG. 10 is a micrograph showing a representative Nissl-stained coronal brain section twenty days after transplantation. Note that the infrahippocampal location of the silk biopolymer and the implantation channel of the stimulating electrode are located in the same anterior-posterior plane.

The ADD was averaged according to session number (N=6 stimulations, each) and treatment target dose (0, 40, 200, and 1000 ng adenosine/day). During the first three sessions a dose-dependent reduction of the ADD became evident. From session four onwards ADDs from recipients of target doses of 40 ng and 200 ng adenosine/day were similar to those from sham controls (0 ng adenosine/day), being consistent with the decline in adenosine released from these polymers with time (Table 3). Remarkably, afterdischarges remained significantly reduced throughout the whole experiment in recipients of polymers releasing a target dose of 1000 ng adenosine/day. At that time the ADD of recipients of target doses of 0 ng, 40 ng, and 200 ng adenosine/day had reached a plateau with average values exceeding 120 s, whereas the ADD of recipients of target doses of 1000 ng adenosine per day remained reduced with values of <100 s. Thus, the behavioral seizure response as observed in FIG. 4 was closely paralleled by the duration of afterdischarges in respective EEGs. These results also indicate that a target dose of 1,000 ng adenosine per day has the potential for prolonged seizure suppression, even if the rates of adenosine release decline with time. After completion of seizure monitoring all animals were sacrificed at day 20 after polymer implantation and subjected to gross histological analysis. In coronal brain sections we detected a cavity resulting from the polymer deposited within the infrahippocampal fissure and traces of the electrode insertion were found in correct locations (FIG. 10). No obvious since for inflammation or bleeding were found.

Example 10

Implant Design and Fabrication

Implants designed to deliver the target doses 0 (=control) or 1,000 ng adenosine per day were designed and fabricated as described previously (Wilz et al., 2008). Briefly, implants were designed to split the target drug load evenly between microspheres and macroscale films that were integrated into a single implant and capped with silk films. Adenosine containing microspheres were prepared according to the MeOH based protocol described previously (Wang et al., 2007a). Water-based porous scaffolds were prepared as previously described (Kim et al., 2005) using the mixture of microspheres and silk solution to imbed the microspheres in the final porous scaffold. To obtain the desired implant geometry (0.6-0.7 mm diameter, 3 mm length), scaffolds were punched out with a 1 mm Miltex biopsy punch and then trimmed with a razor on either end. The porous scaffolds were next coated with multiple macroscale adenosine-loaded silk films comparable to the films described previously (Hofmann et al., 2006). After drug loading, all implants were coated with multiple silk-based capping layers to delay burst-release of adenosine.

Example 11

In Vitro Adenosine Release Studies

Three implants with a target release dose of 1,000 ng adenosine were characterized for release kinetics in vitro. To evaluate release profiles, implants were immersed in 1 ml of Dulbecco's phosphate buffer, pH 7.2 (PBS) at 37° C. Every 24 hours (or 48 hours after two weeks) the PBS was removed and replaced. Adenosine content in the PBS samples removed from the system was measured using a modified fluorescence assay as previously described (Wojcik & Neff, 1982). The collected PBS sample was transferred to a 1.5 ml Eppendorf tube and chloroacetaldehyde was added to a final concentration of 220 µM chloroacetaldehyde. Boiling of mixed adenosine and chloroacetaldehyde for 20 min yielded the fluorescent derivative $1,N^6$-ethenoadenosine. The fluorescence of the sample was measured with a plate reader (excitation=310 nm, emission=410 nm (Rosenfeld & Taylor, 1984). For each device at each time point, three fluorescence readings were taken and averaged.

Example 12

Kindling

Bipolar, coated, stainless steel electrodes (0.20 mm in diameter, Plastics One, Roanoke, Va.) were implanted into the right hippocampus and fixed with a head-set of dental acrylate. Coordinates for the hippocampal electrodes were (tooth bar at 0): 5.0 mm caudal to bregma, 5.0 mm lateral to midline, and 7.5 mm ventral to dura.

Experiment 1

Four days after surgery, the animals were stimulated unilaterally six times every second or third day with a Grass S-88 stimulator (1-ms square-wave pulses of 5 V at 50-Hz frequency for 10 s, 30-min interval between stimulations; these stimulations corresponded to about 350 µA, whereas the afterdischarge thresholds before kindling were in the range of 115 µA).

Behavioral seizures were scored according to the scale of Racine (Racine, 1978). The electroencephalogram (EEG) was recorded for periods of 1 min before and 5 min after application of each stimulating pulse using a Nervus EEG monitoring system. Stimulations on each day were discontinued whenever a stage 5 seizure on that day was reached. Eventually, all animals reacted with a stage 5 seizure at the first (and then only) daily stimulation. After three stage 5 seizures elicited by the first stimulation on three subsequent kindling-days animals were considered to be fully kindled (i.e. reproducibility of stage 5 seizure activity after stimulation). Next, responsiveness to adenosine A1R activation was tested by injection of 2-chloro-N(6)-cyclopentyladenosine (CCPA; adenosine A1-receptor subtype selective agonist). Injection of CCPA (3 mg/kg i.p. in saline containing 20% DMSO) delivered the next day 30 min prior to a test stimulation resulted in complete seizure suppression. Twenty-four (24) hr later, the animals were stimulated again to demonstrate consistency and maintenance of stage 5 seizure activity after stimulation. Only animals that fulfilled these stringent kindling criteria were used for the subsequent experiments.

Polymers were implanted into these fully kindled animals. Implant recipients received one test-stimulation each on day 4, 6, 10, 14, 18, and 21 after polymer implantation and were then subjected to histological analysis.

Experiment 2

Polymer implantation (see below) was combined with electrode implantation (see above) in the same surgery. Experiment 2a: Kindling was initiated four days after polymer implantation with the animals receiving 6 kindling stimulations (1-ms square-wave pulses of 5 V at 50-Hz frequency for 10 sec, 30-min interval between stimulations) each on day 4, 6, 8, and 11 after implantation; this amounted to a total of 24 stimulations. One day after delivery of the 24th stimulus, all animals were treated with 8-cyclopentyl-1,3-dipropylxanthine (DPCPX, adenosine A1-receptor subtype selective antagonist) 30 min prior to stimulation (1 mg/kg, i.p. in DMSO). Twenty-four (24) hr after this drug test all animals were stimulated again once before being sacrificed for histological analysis. Experiment 2b (FIG. 3): Kindling was initiated four days after polymer implantation with the animals receiving six kindling stimulations each on days 4, 5, 6, 7, and 8, after implantation; this amounted to a total of 30 stimulations. In these incompletely kindled adenosine-implant recipients further stimulations were suspended until adenosine release from the polymers had expired (from day eighteen onwards). Kindling stimulations were resumed on days 18, 19, 20, 21, and 22 after implantation (6 stimulations/day; total of 30 additional stimulations). Afterwards the animals were sacrificed for histological analysis.

Example 13

Polymer Implantation

Polymers with a target release rate of 1000 ng adenosine per day or respective control polymers (0 ng adenosine) were implanted using a stereotactic implantation device (internal diameter 0.7 mm, external diameter 1 mm) as described (Boison et al., 2002). The polymers were either implanted after completion of kindling (Experiment 1) or before the onset of kindling (Experiment 2). The polymer-loaded device was stereotactically inserted into the brain using a drill hole above the left hemisphere 2 mm rostral to bregma and 1.6 mm lateral to the midline. Using this drill hole the loaded device was inserted into the brain using an angle of 47° from vertical and an angle of 47° from midline. Thus, a diagonal injection tract was created aiming at a coordinate of 5.0 mm caudal to bregma, 5.0 mm to the right of the midline and 7.5 mm below the dura. Upon reaching the target site the 3 mm long polymer was released and deposited within the infrahippocampal fissure by slowly retracting the outer tube of the device. Finally, the device was fully retracted as described previously (Boison et al., 2002). Thus, the implanted polymers were deposited within a formed cavity of 3 mm length within the right infrahippocampal fissure and adjacent to the electrode implantation site. The diagonal implantation approach pursued here and previously (Li et al., 2007b; Li et al., 2008; Wilz et al., 2008) is characterized by a number of important advantages: (i) Coverage of 3 mm of the dorso-ventral extent of the hippocampus by placement of the implants into the infra-hippocampal fissure; (ii) Minimization of damage to the ipsilateral hippocampus; (iii) Compatibility with the electrode-containing head-set of the animals.

Example 14

Histology and Sample Degradation

Rats were transcardially perfused with 4% paraformaldehyde in phosphate buffer (0.15 M, pH 7.4). To characterize the gross anatomy of the brain at the site of implantation and to confirm implant location, whole rat brains were sectioned (10 μm to 40 μm) either in the coronal or in the sagittal plane and stained with either Cresyl violet, or with hematoxylin and eosin. Scaffold morphology was determined post-implantation by retrieval from the brains with tweezers and sectioned, or the scaffolds were sectioned while still imbedded in the brain tissue. Scaffolds pre-implantation and samples harvested after implantation were washed in PBS, and fixed in 10% neutral buffered formalin before histological analysis. Samples were dehydrated through a series of graded alcohols, embedded in paraffin and sectioned at 5 μm thickness. Sections were stained with either hematoxylin and eosin (H&E) or Cresyl violet (methyl violet 10B).

Samples of implants before and after implantation were compared for degradation. Sections were examined under a Zeiss Axiovert S100 light microscope with a Sony Exwave HAD 3CCD color video camera. The ratio of total surface area of pores (in pixels) to total surface area of the implant (in pixels) was evaluated using Image J image processing software. In this manner, sample porosity was determined by Image J analysis, reflecting the ratio of the total surface area of pores to the total surface area of the implants. Data presented in Table 4 are from six representative adenosine-loaded polymers before or four weeks after transplantation into rat brain. Data were analyzed with a two sample t-test: t=5.08, df=10, p<0.001.

TABLE 4

Sample porosity before and after implantation

|  | Pre-implantation | Post-implantation |
|---|---|---|
| Polymer #1 | 33.9 | 51.2 |
| Polymer #2 | 30.4 | 52.6 |
| Polymer #3 | 48.1 | 52.8 |
| Polymer #4 | 43 | 46.4 |
| Polymer #5 | 48 | 46.7 |
| Polymer #6 | 43 | 55.8 |
| Average | 41.1 | 50.9 |
| Standard Deviation | 7.4 | 3.7 |

Example 15

Statistics

In the in vitro studies standard deviations were calculated for the three repetitions per group by averaging three fluorescence readings per implant. In vivo seizure data are based on N=5 to 8 rats depending on experimental design and experimental group. Individual seizure scores were pooled and averaged for each stimulation in each experimental group. Errors are given as ±SD and data were analyzed using two way ANOVA on ranks followed by a Bonferroni test.

Example 16

Adenosine Release Profiles

Figure 3A:
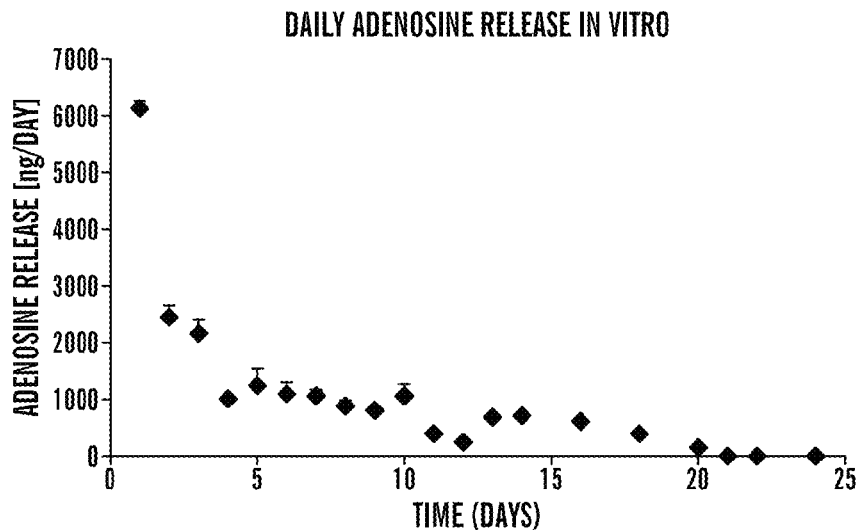
FIG. 3 presents data reflecting the daily release of adenosine from silk-based polymers. Panel (A) Adenosine release in vitro was determined for each day shown, based on averaged values from N=3 polymers. Note the stable release rate of around 1000 ng adenosine/day from day 4 to day 10, corresponding to the pre-designed target release rate. Errors are given as ±SD. Panel (B) Assessment of antiepileptogenesis in the rat kindling model according to Silver et al., 29 Ann. Neurol. 356-63 (1991). Kindling is initiated during drug delivery followed by a washout period of the drug; subsequently, kindling is resumed in the absence of the drug. Note that the criterion for complete suppression of epileptogenesis is a shift of the kindling curve to the right; the number of drug-free kindling stimulations needed to trigger a specific seizure stage should be the same as in control animals. Black: no seizure suppression, no antiepileptogenesis; dark gray: untreated control animal; gray: seizure suppression plus partial antiepileptogenesis; light gray: complete antiepileptogenesis; lightest gray: seizure suppression, no antiepileptogenesis.

The daily dose of adenosine released from the adenosine-loaded polymers (ADO-polymers) was determined by fluorescence analysis of adenosine after derivatization to 1,$N^6$-ethenoadenosine. After an initial burst in adenosine-release (>2000 ng/day) during the first three days of incubation, the polymers were characterized by a stable release rate of around 1000 ng/day (1019±197) between day four and day ten (FIG. 3A). After this stable release period, daily rates of adenosine release rapidly dropped to 414±59 ng adenosine at day eleven and 256±45 ng at day twelve. Polymers ceased to release adenosine within a time frame of twenty-one days of incubation. In contrast, no adenosine was detectable in supernatants from cultured control polymers. This unique release profile of high and stable initial release rates (1000 ng/day) followed by gradual expiration of adenosine release allowed confirmation that the adenosine-dependence of implant-mediated therapeutic effects.

Experiment 1 studied the antiictogenic effects of polymer-based adenosine release, after the polymers were implanted into fully kindled rats. Given the high initial adenosine-release rate from the ADO-polymers it was expected that initial complete protection from seizures followed by a gradual recurrence of seizure activity in parallel with the decline in therapeutic adenosine release.

Figure 3B:
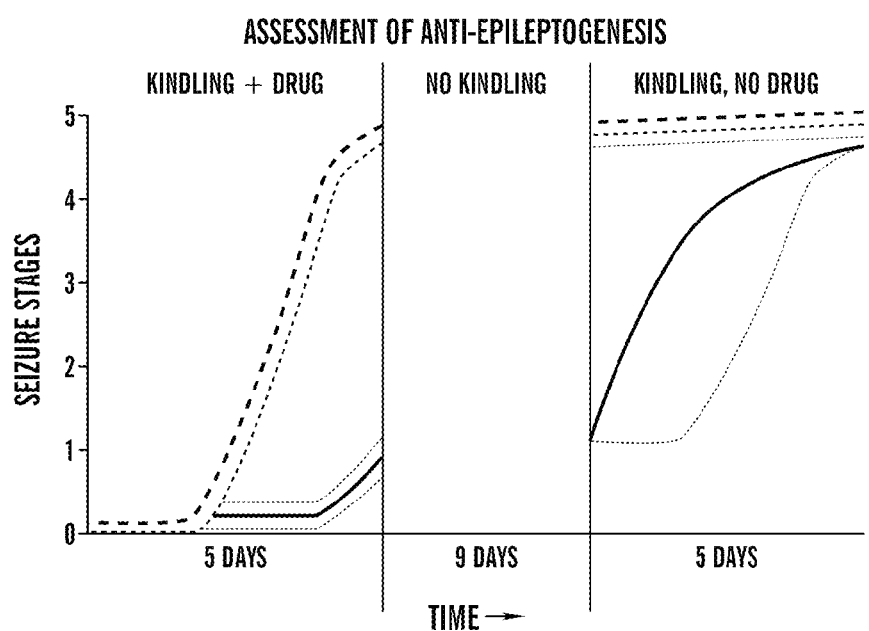

Experiment 2 (schematically depicted in FIG. 3B) studied the unique release profile of adenosine and assessment of antiictogenic and anti-epileptogenic effects of polymer-based adenosine release. Here, polymers were implanted four days prior to kindling initiation. The expectation is reduced kindling development in the ADO-polymer treated group of rats. Suppression of kindling development can either be due to true suppression of epileptogenesis, or "just" to suppression of seizures. In the latter case adenosine-mediated seizure suppression would "mask" any anti-epileptogenic effects. To distinguish among these two possibilities an experimental paradigm first described by McNamara (Silver et al., 29 Ann. Neurol. 356-63 (1991) was adopted: ADO-polymer and control-polymer recipients were kindled only until the ADO-group showed first signs of kindling (FIG. 3B); during that same time frame animals from the control group are expected to be fully kindled; this period of initial kindling during a period of constant adenosine release in the ADO-group (1000 ng adenosine per day during days 4 to 8 after polymer implantation) was followed by a 9-day gap in kindling. During this gap in kindling, the polymers ceased to release significant amounts of adenosine. Kindling was then resumed in both groups. In case that adenosine in the ADO-polymer group had merely suppressed seizures but not epileptogenesis, one expects a "jump" in seizure expression, i.e., seizure stages should be similar to those observed in the control group (FIG. 3B). In contrast, if polymer-based adenosine-release had suppressed epileptogenesis, one expects that kindling development resumes, where it was discontinued previously, i.e., the seizure stage curve in the second kindling phase of the ADO-polymer group, should be parallel to the seizure stage curve in the initial kindling phase of the control group. Using this paradigm, the number of drug-free afterdischarges to reach a particular kindling stage should be the same in case of complete antiepileptogenesis (FIG. 3B); if the number of drug-free afterdischarges in the drug-treated group is less than in the control group (FIG. 3B), some epileptogenesis took place during drug administration (Silver et al., 1991).

Experiment 1

Figure 6:
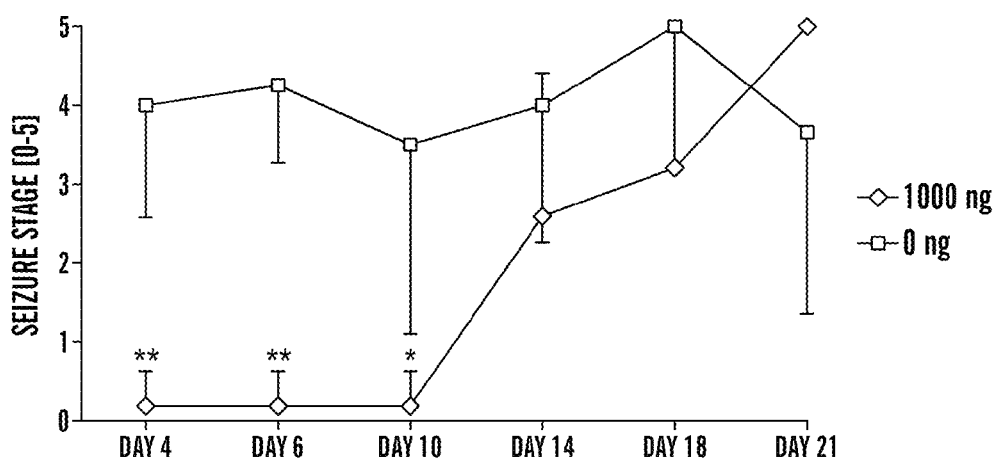
FIG. 6 presents the suppression of fully kindled seizures by implant-derived adenosine. Fully kindled rats (criterion: at least three consecutive stage 5 seizures) received infrahippocampal implants of silk-based polymers with a daily target release rate for adenosine of 0 ng (N=4, squares), or 1000 ng (N=5, diamonds). Individual test stimulations were delivered at days 4, 6, 10, 14, 18, and 21. Seizure stages, averaged across animals from each group, are shown for every stimulus. Note that recipients of a target dose of 1000 ng adenosine per day are completely protected from any seizures during the 10 days after implantation corresponding to sustained release of adenosine during that time period. Errors are given as ±SD. Data were analyzed by two way ANOVA followed by a Bonferroni test; the significance of interaction between groups was determined as $F=2.390$; $P<0.05$; significance levels of individual tests is indicated: * $P<0.05$, ** $P<0.01$.

Suppression of kindled seizures by polymer-based adenosine release. To establish the anti-ictogenic potential of silk-polymer based release of adenosine, either adenosine releasing polymers (FIG. 3A) (n=5) or corresponding control polymers (n=4) that were not loaded with adenosine were implanted into the infrahippocampal fissure of fully kindled rats. Before polymer implantation all rats reproducibly reacted with stage 4 or 5 seizures following stimulation and thus met our stringent kindling criteria. Animals received one test stimulus each at days 4, 6, 10, 14, 18, and 21 after polymer implantation. Recipients of control polymers maintained the expression of convulsive seizures (averaged seizure stage of 3.9±1.6) during the course of the experiments, but recipients of implants releasing 1000 ng adenosine/day were initially almost completely protected from any seizures (averaged seizures stage of 0.2±0.5 until day ten after implantation) (FIG. 6). During this time, 4 out of 5 rats did not express any seizures (stage 0), while the remaining rat expressed non-convulsive stage 1 seizures. In line with reduced levels of adenosine released from the polymers from day ten onwards (FIG. 3A), seizure activity in the adenosine group gradually resumed (FIG. 6) indicating that seizure suppression was due to implant-dependent adenosine release. To further confirm that seizure suppression is due to implant-derived adenosine an ADO-polymer treated rat received an intraperitoneal injection of the adenosine A1R antagonist DPCPX (1 mg/kg, i.p.) at day three. When tested before or after DPCPX on days 2 and 4, the rat was protected from seizures (stage 0). Thirty (30) min after injection of DPCPX on day three, however, a stage-5 seizure was elicited indicating adenosine-dependence of seizure suppression. Together, these results suggest a powerful anti-ictogenic activity of focal implant derived-adenosine release in the range of 1000 ng per day.

Experiment 2

Figure 8A:
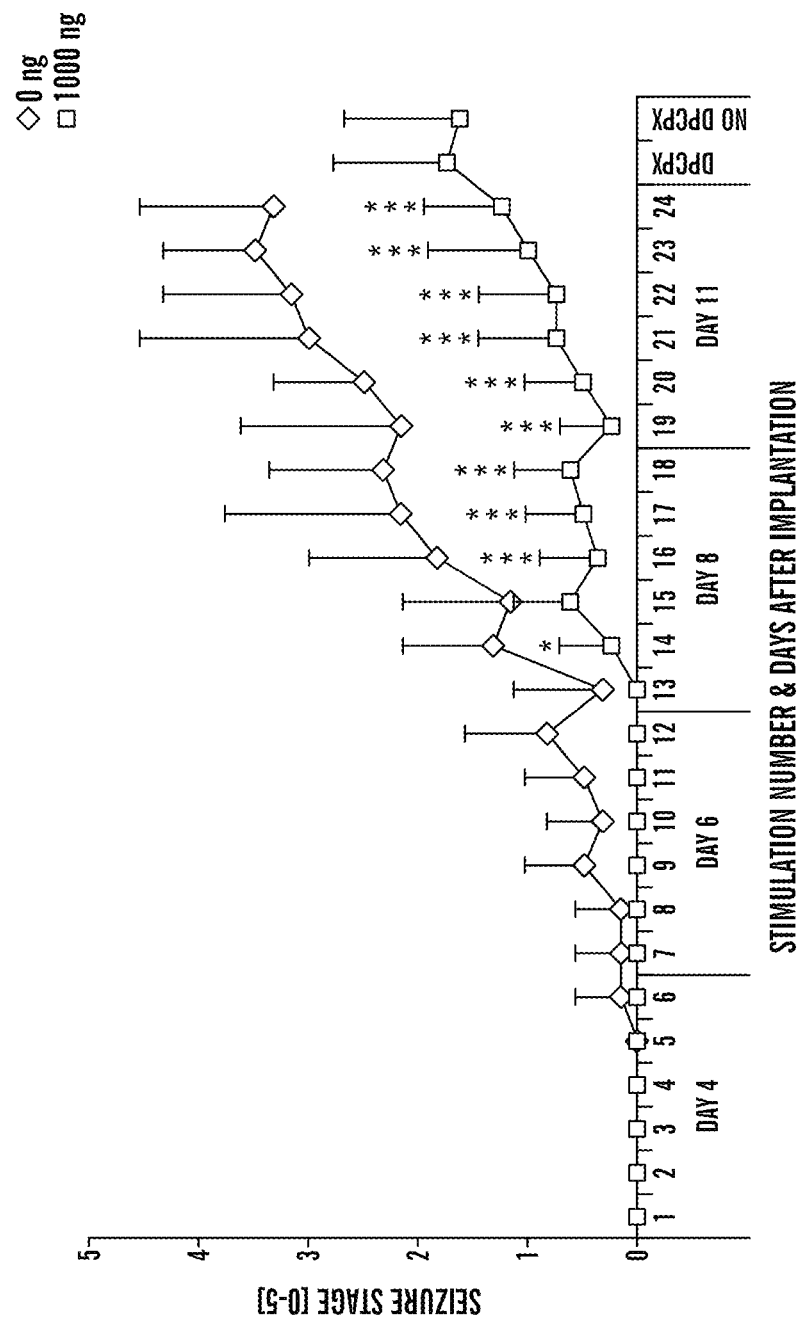
FIG. 8A: Four days after infrahippocampal implantation of silk-based polymers with daily target release rates for adenosine of 0 ng (N=5, diamond), or 1000 ng (N=8, square) kindling stimulations were delivered at a rate of 6 stimulations/day on days 4, 6, 8, and 11 following implantation. A total of twenty-four kindling stimulations were delivered. On day twelve, DPCPX (1 mg/kg, i.p.) was injected 30 min prior to stimulation. Each animal was tested again on day thirteen (no DPCPX). Seizure stages were averaged across animals from each group for each individual stimulus. Note that recipients of a target dose of 1000 ng adenosine/day displayed significant protection from kindling development, and DPCPX did not increase the seizure score. Errors are given as ±SD. Data were analyzed by two way ANOVA followed by a Bonferroni test; the significance of interaction between groups was determined as $F=6.704$, $P<0.0001$; significance levels of individual tests are indicated: * $P<0.05$,  $P<0.01$, * $P<0.001$.

Suppression of epileptogenesis by polymer-based adenosine release To separate experiments were performed to investigate the possibility for anti-epileptogenic effects of polymer-based adenosine release. In Experiment 2a implanted kindling electrodes and polymers (target release rate of 1000 ng adenosine/day, n=8; and control polymers, n=6) into adult male SD-rats at day 0. The animals received 4×6 kindling stimulations delivered on days 4, 6, 8, and 11 after polymer implantation; according to adenosine release data (FIG. 3), the first 18 stimulations were given during a time frame of almost constant release of 1000 ng adenosine/day, while adenosine release at day eleven (stimulation 19 to 24) had dropped to about 400 ng adenosine per day. On day twelve, each of the adenosine-implant recipients received a single injection of the A1R antagonist DPCPX (1 mg/kg, i.p.), followed after 30 min by a single test stimulation. On day thirteen, each of these animals was tested again in the absence of DPCPX. These results (FIG. 8A) demonstrate complete suppression of kindling development during the first 13 stimulations in the adenosine group, despite the regular presence of afterdischarges and wet dog shakes, elicited by the test stimulations.

Compared to control implant recipients, the adenosine implant recipients continued to display a significant suppression of kindling epileptogenesis during the course of this experiment. Only at day eleven, corresponding to a drop of implant-derived adenosine-release, kindling development started to progress in the ADO-group. At stimulation 24 the averaged seizure response of the adenosine implant recipients (stage 1.25±0.7) was significantly ($P<0.001$) lower than the seizure response observed in the control group (stage 3.3±1.2). To determine whether seizure suppression was due to suppression of ictogenesis (by implant-derived adenosine activating A1Rs) or due to suppression of epileptogenesis, stimulation #25 was given in the presence of DPCPX. The resulting seizure response (stage 1.8±1.0) was only slightly different from the preceding seizure response #24 (stage 1.25±0.7; $P=0.05$) and not different from the subsequent seizure response #26 elicited on day later (stage 1.6±1.1; $P=0.3$). Whereas DPCPX, paired with kindling stimulations, readily elicits stage 5 seizures in fully kindled rats that are otherwise protected from adenosine releasing brain implants (Boison et al., 43 Epilepsia 788-96 (2002); Güttinger et al., 193 Exp. Neurol. 53-64 (2005); Huber et al., 98 P.N.A.S. USA 7611-16 (2001)), in the present study test stimulations in the presence of DPCPX failed to elicit control group-like seizures. These results indicate that reduced seizure scores in adenosine-releasing implant recipients might be related to anti-epileptogenic effects of the adenosine-releasing brain implants.

Figure 8B:
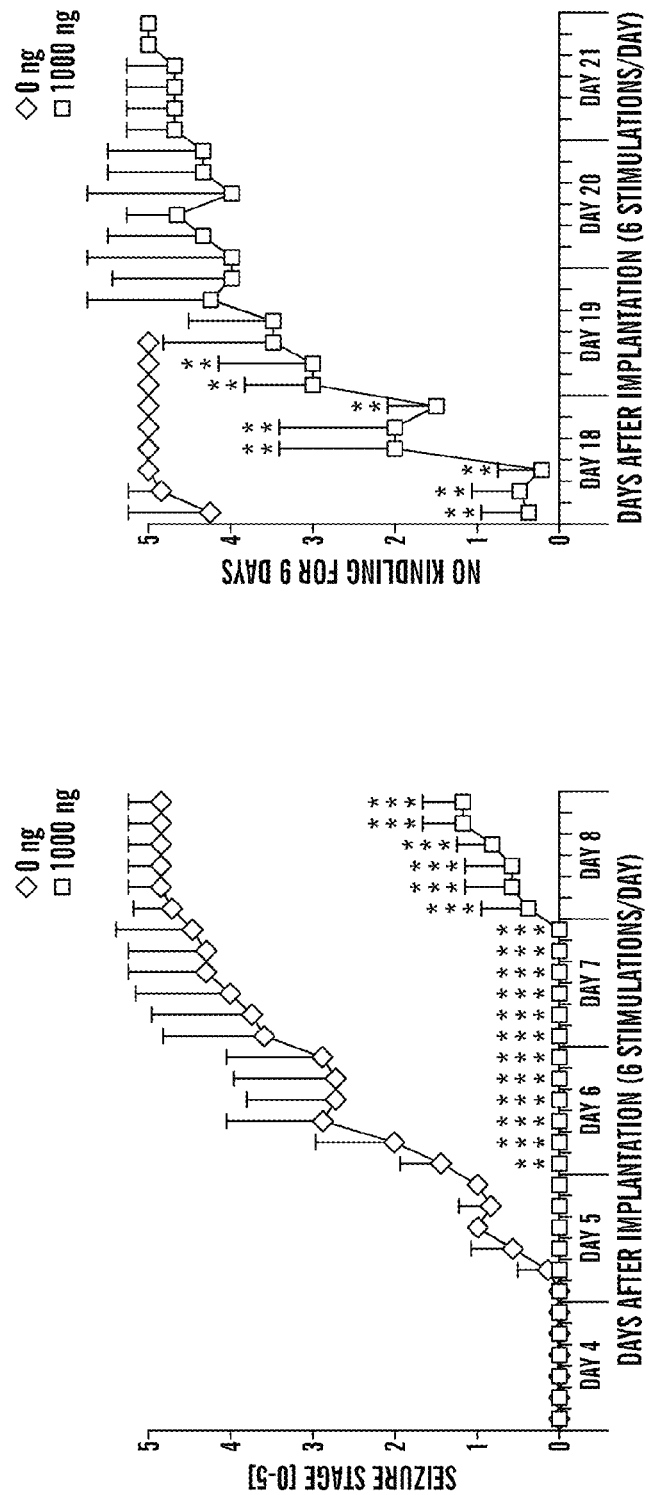
FIG. 8B shows that four days after infrahippocampal implantation of silk-based polymers with daily target release rates for adenosine of 0 ng (N=7, diamond), or 1000 ng (N=5, square) kindling stimulations were delivered at a rate of 6 stimulations/day on days 4, 5, 6, 7, and 8 following implantation. A total of 30 kindling stimulations were delivered. Note the increased kindling frequency compared to FIG. 8A. After the 30th kindling stimulation, kindling was discontinued for nine days. Kindling stimulations were resumed at day 18. Seizure stages were averaged across animals from each group for each individual stimulus. Note that recipients of a target dose of 1000 ng adenosine per day resumed kindling at day 18 at a level at which kindling was discontinued at day eight. After 7 consecutive stage 5 seizures, kindling was discontinued in control animals due to animal welfare considerations. Errors are given as ±SD. Data were analyzed by two way ANOVA followed by a Bonferroni test; the significance of interaction between groups was determined as $F=19.36$, $P<0.0001$; significance levels of individual tests are indicated:  $P<0.01$, * $P<0.001$.
Figure 9:
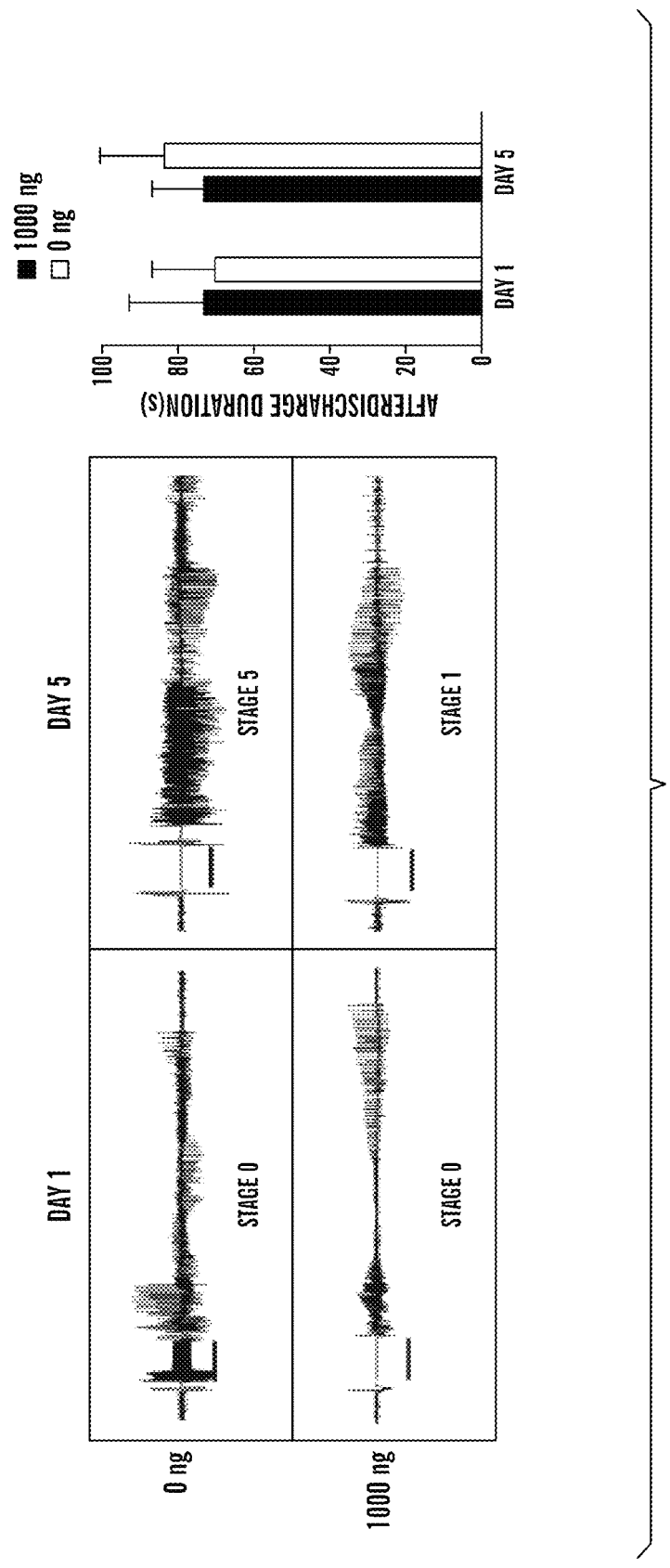
FIG. 9 presents after-discharges during kindling acquisition. Representative EEG recordings are shown from control polymer recipients (0 ng) and adenosine implant recipients (1000 ng) on day 1 and 5 of kindling (corresponding to day 4 and day 8 after polymer implantation). The scale bar represents the 10 second stimulation interval. Note the presence of electrographic after-discharges in the adenosine implant recipients. The after-discharge duration (ADD) on day 1 and 5 of kindling was determined after each kindling-stimulation by analyzing the respective EEG recordings. ADDs were averaged for each day (n=6 stimulations) and treatment type: implants releasing target doses of 0 ng adenosine (N=7) or 1000 ng (N=5) adenosine per day. Errors are given as ±SD. Data were analyzed by ANOVA; ADDs were not statistically different, P>0.05.

To further study possible anti-epileptogenic effects of adenosine, Experiment 2b (FIG. 3B), paired kindling stimulations with the specific adenosine-release profile of the polymers. Two groups of rats were implanted with adenosine-releasing (n=5) or control polymers (n=7) at the day of electrode implantation. The first set of 30 kindling stimulations was delivered during a time-window during which the polymers afforded a stable release rate of 1000 ng adenosine/day (day four to eight, 6 stimulations per day). In these pre-kindled rats kindling was resumed after a gap of nine days, with the aim to deliver additional stimulations during the expiration phase of the polymers (day eighteen to twenty-one) until all animals were fully kindled. In line with findings from Experiment 2a, recipients of adenosine-releasing implants showed robust suppression of kindling development (FIG. 8B) during the first five days of stimulation. Even after 30 stimulations these animals continued to be protected from convulsive seizures and reacted with an average seizure score of $1.3\pm0.5$ at the eighth day after polymer implantation. In contrast, recipients of control implants kindled the same way reacted reproducibly with stage 4 or 5 seizures at that time point (average seizure score of $4.9\pm0.4$ at stimulation 30 at the eighth day after polymer implantation). After this initial seizure assessment, the animals were not subjected to any further stimulation during the following nine days. Kindling was resumed at day eighteen, when all control animals continued to display stage 4 and 5 seizures. In contrast, kindling in adenosine-releasing polymer recipients resumed with stage 0 to 1 scores (average score of $0.5\pm0.6$) at a level similar to the seizure scores when kindling was discontinued (FIG. 8B).

Subsequently, these animals responded with gradual increases in seizure severity until they reached stage 4 to 5 scores at day twenty and twenty-one after polymer implantation. This kindling curve was parallel—albeit shifted to the right—to the kindling curve of recipients of control implants. The number of drug-free afterdischarges in ADO-treated rats to elicit seizure stages comparable to those of control animals was lower than in those control rats, however, indicating that some epileptogenesis had occurred during the phase of adenosine delivery (Silver et al., 1991). Together, experiments 2A and 2B suggest that focal adenosine delivery exerts partial antiepileptogenic effects.

Example 17

The Focal Release of Adenosine does not Affect the Expression of Afterdischarges To rule out the possibility that the stimulus delivered to adenosine-implant recipients was insufficient to trigger epileptogenesis in the presence of this inhibitory modulator, electrographic afterdischarges in recipients of adenosine-releasing or control implants were quantified at the onset of kindling and during the 5th day of kindling (i.e. day eight after polymer implantation), a time point at which control animals were almost fully kindled, while adenosine-implant recipients did not proceed beyond stage 1 seizures. the data (FIG. 9) demonstrate that during day 1 of kindling (=day four after polymer implantation) afterdischarge durations in both groups of animals were initially almost identical ($71\pm16$ sec in control animals vs. $73\pm20$ sec in recipients of ADO polymers; $P>0.05$). These data indicate that adenosine-release from the polymers did not affect the expression of epileptogenic afterdischarges. Afterdischarge durations in ADO polymer recipients remained fairly constant during the first five days of kindling. Averaged afterdischarge durations during the fifth day of kindling amounted to $73\pm14$ sec (FIG. 9) in the ADO group, whereas the afterdischarge duration in the control group had increased to $84\pm17$ sec.

Example 18

Degradation of Silk-Based Brain Implants after Four Weeks In Vivo

The adenosine release kinetic described above and the time-restricted therapeutic efficacy of the implants used in the current study suggested high and consistent initial release rates of adenosine coupled to degradation of the implants over time. Therefore, the adenosine-releasing silk-based polymers were subjected to a rigorous analysis to assess possible degradation processes. Sections (5 µm) of adenosine-loaded polymers before transplantation, or retrieved after four weeks in vivo (N=6, each), were subjected to an Image J analysis to calculate the ratio of the total surface area of pores (in pixels) to the total surface area of the implant (in pixels) (FIGS. 11A, 11B). Prior to implantation, the average silk implant porosity based on surface area analysis was 41.1%, and this increased to 50.9% after implantation (Table 4, Example 14, above). The silk implants on average exhibited 9.8% more pore surface area after four weeks in vivo, suggesting that degradation of the polymers was occurring in the rat brain. After completion of the in vivo experiments all rat brains were subjected to histological analysis to verify electrode and polymer location. Four weeks after implantation, the partly degraded polymers were still located in close proximity to the stimulated hippocampus (FIG. 11C). Closer inspection of the implants (FIG. 11D) revealed signs of degradation based on the loss of structural integrity of the scaffolds.

The invention claimed is:

1. A biocompatible, biodegradable, sustained-release implantable pharmaceutical composition comprising adenosine in a silk fibroin-based, sustained-release delivery system, wherein the silk fibroin-based, sustained delivery system comprises adenosine-encapsulating microspheres embedded in a silk fibroin scaffold and wherein the scaffold further comprises adenosine which is not encapsulated in the microspheres, wherein upon implantation said implantable pharmaceutical composition has been shown in reference subjects to release from about 200 ng adenosine per day to about 10 mg adenosine per day, inclusive, for at least eight consecutive days.

2. The biocompatible, biodegradable sustained-release implantable pharmaceutical composition of claim 1, wherein upon implantation said implantable pharmaceutical composition has been shown in reference subjects to release from about 800 ng adenosine per day to about 1100 ng adenosine per day, inclusive, for at least eight consecutive days.

3. The biocompatible, biodegradable sustained-release implantable pharmaceutical composition of claim 1, wherein upon implantation said implantable pharmaceutical composition has been shown in reference subjects to release from about 200 ng adenosine per day to about 5 mg adenosine per day, inclusive, for at least eight consecutive days.

4. The biocompatible, biodegradable sustained-release implantable pharmaceutical composition of claim 1, wherein upon implantation, the implantable composition has been shown in reference subjects to release from about 1 mg adenosine per day to about 10 mg adenosine per day, inclusive, for at least eight consecutive days.

5. The biocompatible, biodegradable sustained-release implantable pharmaceutical composition of claim 1, wherein upon implantation, the implantable composition has been shown in reference subjects to release about 1 mg adenosine per day for a time span of ten days.

6. The biocompatible, biodegradable sustained-release implantable pharmaceutical composition of claim 1, wherein about one-third of the total adenosine in the composition is encapsulated in the microspheres.

7. The biocompatible, biodegradable sustained-release implantable pharmaceutical composition of claim 1, wherein the scaffold comprises one or more silk fibroin coating layers comprising adenosine.

8. The biocompatible, biodegradable sustained-release implantable pharmaceutical composition of claim 1, wherein the scaffold comprises one or more silk fibroin coating layers which comprise no added adenosine.

9. A method of treating epilepsy or preventing epileptogenesis in a subject in need thereof comprising administering directly to the brain of the subject a pharmaceutical composition comprising adenosine in a silk fibroin-based, sustained-release delivery system, wherein the silk fibroin-based, sustained delivery system comprises adenosine-encapsulating microspheres embedded in a silk fibroin scaffold and wherein the scaffold further comprises adenosine which is not encapsulated in the microsphere.

10. The method of claim 9, wherein said delivery system has been shown in reference subjects to release from about 50 ng adenosine per day to about 50 mg adenosine per day, inclusive.

11. The method of claim 10, wherein said delivery system has been shown in reference subjects to release from about 200 ng adenosine per day to about 5 mg adenosine per day, inclusive.

12. The method of claim 10, wherein said delivery system has been shown in reference subjects to release at least about 1 mg adenosine per day to about 10 mg adenosine per day, inclusive.

* * * * *